(12) United States Patent
Bachman et al.

(10) Patent No.: US 9,636,117 B2
(45) Date of Patent: May 2, 2017

(54) DEVICES, SYSTEMS AND METHODS FOR ENCLOSING AN ANATOMICAL OPENING

(71) Applicant: Pulsar Vascular, Inc., San Jose, CA (US)

(72) Inventors: Anthony Bachman, San Jose, CA (US); Chad Roue, San Jose, CA (US); Marc Jensen, San Jose, CA (US); Mike Walsh, San Jose, CA (US); Scott Cameron, San Jose, CA (US); Michael Gendreau, San Jose, CA (US); Robert M. Abrams, Los Gatos, CA (US)

(73) Assignee: PULSAR VASCULAR, INC., San Jose, CA (US)

( * ) Notice: Subject to any disclaimer, the term of this patent is extended or adjusted under 35 U.S.C. 154(b) by 0 days.

(21) Appl. No.: 14/808,343

(22) Filed: Jul. 24, 2015

(65) Prior Publication Data

US 2015/0327867 A1    Nov. 19, 2015

Related U.S. Application Data

(62) Division of application No. 13/646,602, filed on Oct. 5, 2012, now Pat. No. 9,119,625.
(Continued)

(51) Int. Cl.
*A61B 17/12* (2006.01)

(52) U.S. Cl.
CPC .............................. *A61B 17/12118* (2013.01)

(58) Field of Classification Search
CPC ........ A61B 17/12118; A61B 17/12145; A61B 17/12113; A61B 17/12; A61M 29/00
See application file for complete search history.

(56) References Cited

U.S. PATENT DOCUMENTS 3,868,956 A   3/1975  Alfidi et al.
4,164,045 A   8/1979  Bokros et al.
(Continued)

FOREIGN PATENT DOCUMENTS

AU     2006304660 A1    4/2007
CN         1384726      12/2002
(Continued)

OTHER PUBLICATIONS

Polytetraflouroethylene Implants, DermNet NZ, Nov. 11, 2005, http://dermetnz.org/polytetrafluoroethylene.html.
(Continued)

*Primary Examiner* — Victor Nguyen
(74) *Attorney, Agent, or Firm* — Troutman Sanders LLP

(57) ABSTRACT

The present technology is directed generally to devices, systems, and methods for enclosing anatomical openings. In several embodiments, an aneurysm device is endovascularly deliverable to a site proximate to an arterial aneurysm. The aneurysm device includes a closure structure having a distal-facing aspect configured to at least partially occlude the aneurysm and a proximal-facing aspect configured to arch over lumina of an artery. The device further includes a supplemental stabilizer connected to the closure structure and configured to reside in the artery and press outward against a luminal wall thereof. In some embodiments, the device can also include a barrier spanning at least a portion of the distal-facing aspect of the closure structure and configured to further occlude a neck of the aneurysm. In further embodiments, the closure structure can be configured to restrict and/or divert flow to or from the aneurysm.

12 Claims, 16 Drawing Sheets

Related U.S. Application Data

(60) Provisional application No. 61/543,785, filed on Oct. 5, 2011.

(56) References Cited

U.S. PATENT DOCUMENTS

| | | |
|---|---|---|
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta et al. |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi et al. |
| 5,226,911 A | 7/1993 | Chee et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A | 6/1996 | Purdy |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,980,554 A | 11/1999 | Lenker et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A * | 3/2000 | Abrams ........... A61B 17/12022 606/200 |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,041 B1 | 2/2002 | Kupiecki et al. |
| 6,344,048 B1 | 2/2002 | Chin et al. |
| 6,361,558 B1 | 3/2002 | Hieshima et al. |
| 6,375,668 B1 | 4/2002 | Gifford et al. |
| 6,383,174 B1 | 5/2002 | Eder |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,592,605 B2 | 7/2003 | Lenker et al. |
| 6,613,074 B1 | 9/2003 | Mitelberg et al. |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 | 11/2003 | VanTassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon, Jr. |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |
| 6,746,468 B1 | 6/2004 | Sepetka et al. |
| 6,780,196 B2 | 8/2004 | Chin et al. |
| 6,790,218 B2 | 9/2004 | Jayaraman |
| 6,802,851 B2 | 10/2004 | Jones et al. |
| 6,811,560 B2 | 11/2004 | Jones et al. |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,843,802 B1 | 1/2005 | Villalobos et al. |
| 6,855,153 B2 | 2/2005 | Saadat |
| 6,863,678 B2 | 3/2005 | Lee et al. |
| 6,890,218 B2 | 5/2005 | Patwardhan et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |

(56) References Cited

U.S. PATENT DOCUMENTS

| | | |
|---|---|---|
| 7,147,659 B2 | 12/2006 | Jones |
| 7,156,871 B2 | 1/2007 | Jones et al. |
| 7,169,177 B2 | 1/2007 | Obara |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,306,622 B2 | 12/2007 | Jones et al. |
| 7,322,960 B2 | 1/2008 | Yamamoto et al. |
| 7,343,856 B2 | 3/2008 | Blohdorn |
| 7,387,629 B2 | 6/2008 | Vanney et al. |
| 7,410,482 B2 | 8/2008 | Murphy et al. |
| 7,569,066 B2 | 8/2009 | Gerberding et al. |
| 7,608,088 B2 | 10/2009 | Jones et al. |
| 7,662,168 B2 | 2/2010 | McGuckin, Jr. et al. |
| 7,857,825 B2 | 12/2010 | Moran et al. |
| 7,892,254 B2 | 2/2011 | Klint et al. |
| 8,016,853 B2 | 9/2011 | Griffen et al. |
| 8,075,585 B2 | 12/2011 | Lee et al. |
| 8,187,315 B1 | 5/2012 | Clauson et al. |
| 8,262,692 B2 | 9/2012 | Rudakov |
| 8,388,650 B2 | 3/2013 | Gerberding et al. |
| 8,444,667 B2 | 5/2013 | Porter |
| 8,470,013 B2 | 6/2013 | Duggal et al. |
| 8,540,763 B2 | 9/2013 | Jones et al. |
| 8,545,530 B2 | 10/2013 | Eskridge et al. |
| 8,551,132 B2 | 10/2013 | Eskridge et al. |
| 8,556,953 B2 | 10/2013 | Berez et al. |
| 8,715,312 B2 | 5/2014 | Burke et al. |
| 8,715,338 B2 | 5/2014 | Frid |
| 8,728,141 B2 | 5/2014 | Riina et al. |
| 8,747,430 B2 | 6/2014 | Porter |
| 8,771,341 B2 | 7/2014 | Strauss et al. |
| 8,915,950 B2 | 12/2014 | Cam et al. |
| 8,926,680 B2 | 1/2015 | Ferrera et al. |
| 8,956,399 B2 | 2/2015 | Cam et al. |
| 8,979,893 B2 | 3/2015 | Gerberding et al. |
| 9,060,886 B2 | 6/2015 | Molaei et al. |
| 9,107,670 B2 | 8/2015 | Hannes et al. |
| 9,119,625 B2 | 9/2015 | Bachman et al. |
| 9,179,918 B2 | 11/2015 | Levy et al. |
| 9,186,267 B2 | 11/2015 | Losordo et al. |
| 9,192,388 B2 | 11/2015 | Cam et al. |
| 9,211,124 B2 | 12/2015 | Campbell et al. |
| 9,259,229 B2 | 2/2016 | Abrams et al. |
| 9,277,924 B2 | 3/2016 | Clarke et al. |
| 2002/0026232 A1 | 2/2002 | Marotta et al. |
| 2003/0033003 A1 | 2/2003 | Harrison et al. |
| 2003/0057156 A1 | 3/2003 | Peterson et al. |
| 2003/0139802 A1 | 7/2003 | Wulfman et al. |
| 2003/0181922 A1 | 9/2003 | Alferness |
| 2003/0181942 A1 | 9/2003 | Sutton et al. |
| 2003/0195385 A1 | 10/2003 | DeVore |
| 2003/0195553 A1 | 10/2003 | Wallace et al. |
| 2003/0212412 A1 | 11/2003 | Dillard et al. |
| 2004/0044391 A1 | 3/2004 | Porter |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0158311 A1 | 8/2004 | Berhow et al. |
| 2004/0167597 A1 | 8/2004 | Costantino et al. |
| 2004/0167602 A1 | 8/2004 | Fischell et al. |
| 2004/0172056 A1 | 9/2004 | Guterman et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2005/0021023 A1 | 1/2005 | Guglielmi et al. |
| 2005/0025797 A1 | 2/2005 | Wang et al. |
| 2005/0033409 A1 | 2/2005 | Burke et al. |
| 2005/0096728 A1 | 5/2005 | Ramer |
| 2005/0177224 A1 | 8/2005 | Fogarty et al. |
| 2006/0004436 A1 | 1/2006 | Amarant et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0064151 A1 | 3/2006 | Guterman et al. |
| 2006/0106418 A1 | 5/2006 | Seibold et al. |
| 2006/0200234 A1 | 9/2006 | Hines |
| 2006/0206199 A1 | 9/2006 | Churchwell et al. |
| 2006/0247680 A1 | 11/2006 | Amplatz et al. |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0088387 A1 | 4/2007 | Eskridge et al. |
| 2007/0106311 A1 | 5/2007 | Wallace et al. |
| 2007/0191884 A1 | 8/2007 | Eskridge et al. |
| 2007/0198075 A1 | 8/2007 | Levy |
| 2007/0203567 A1 | 8/2007 | Levy |
| 2007/0270902 A1 | 11/2007 | Slazas et al. |
| 2008/0004653 A1 | 1/2008 | Sherman et al. |
| 2008/0004692 A1 | 1/2008 | Henson et al. |
| 2008/0039930 A1 | 2/2008 | Jones et al. |
| 2008/0147100 A1 | 6/2008 | Wallace |
| 2008/0183143 A1 | 7/2008 | Palasis et al. |
| 2008/0221600 A1 | 9/2008 | Dieck et al. |
| 2008/0269774 A1 | 10/2008 | Garcia et al. |
| 2008/0319533 A1 | 12/2008 | Lehe |
| 2009/0069880 A1 | 3/2009 | Vonderwalde et al. |
| 2009/0125053 A1 | 5/2009 | Ferrera et al. |
| 2009/0306678 A1 | 12/2009 | Hardert et al. |
| 2010/0023105 A1 | 1/2010 | Levy et al. |
| 2010/0063531 A1 | 3/2010 | Rudakov et al. |
| 2010/0094335 A1 | 4/2010 | Gerberding et al. |
| 2011/0022149 A1 | 1/2011 | Cox et al. |
| 2011/0270373 A1 | 11/2011 | Sampognaro et al. |
| 2012/0143237 A1 | 6/2012 | Cam et al. |
| 2012/0143317 A1 | 6/2012 | Cam et al. |
| 2012/0245674 A1 | 9/2012 | Molaei et al. |
| 2012/0290067 A1 | 11/2012 | Cam et al. |
| 2012/0296361 A1 | 11/2012 | Cam et al. |
| 2013/0090682 A1 | 4/2013 | Bachman et al. |
| 2013/0204290 A1 | 8/2013 | Clarke et al. |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304109 A1 | 11/2013 | Abrams et al. |
| 2014/0052233 A1 | 2/2014 | Cox et al. |
| 2014/0058420 A1 | 2/2014 | Hannes et al. |
| 2014/0121752 A1 | 5/2014 | Losordo et al. |
| 2014/0128901 A1 | 5/2014 | Kang et al. |
| 2014/0142608 A1 | 5/2014 | Eskridge et al. |
| 2014/0180377 A1 | 6/2014 | Bose et al. |
| 2014/0236216 A1 | 8/2014 | Gerberding |
| 2015/0039015 A1 | 2/2015 | Gerberding |
| 2015/0142025 A1 | 5/2015 | Brandeis |
| 2015/0142042 A1 | 5/2015 | Cox |
| 2015/0142043 A1 | 5/2015 | Furey |
| 2015/0157329 A1 | 6/2015 | Rudakov et al. |
| 2015/0157331 A1 | 6/2015 | Levy et al. |
| 2015/0164512 A1 | 6/2015 | Chin et al. |
| 2015/0164665 A1 | 6/2015 | Cam et al. |
| 2015/0182361 A1 | 7/2015 | Ferrera et al. |
| 2015/0196305 A1 | 7/2015 | Meyer et al. |
| 2015/0216534 A1 | 8/2015 | Riina et al. |
| 2015/0216687 A1 | 8/2015 | Gerberding et al. |
| 2015/0245932 A1 | 9/2015 | Molaei et al. |
| 2015/0250628 A1 | 9/2015 | Monstadt et al. |
| 2015/0282962 A1 | 10/2015 | Strauss et al. |
| 2015/0342612 A1 | 12/2015 | Wu et al. |
| 2016/0015395 A1 | 1/2016 | Molaei et al. |
| 2016/0015396 A1 | 1/2016 | Cox et al. |
| 2016/0030050 A1 | 2/2016 | Franano et al. |
| 2016/0038153 A1 | 2/2016 | Losordo et al. |
| 2016/0249936 A1 | 9/2016 | Clarke et al. |

FOREIGN PATENT DOCUMENTS

| | | |
|---|---|---|
| CN | 1399530 A | 2/2003 |
| CN | 1399531 A | 2/2003 |
| CN | 101489492 A | 7/2009 |
| CN | 102202585 A | 9/2011 |

(56) References Cited

FOREIGN PATENT DOCUMENTS

| | | |
|---|---|---|
| CN | 102762156 A | 10/2012 |
| CN | 103230290 A | 8/2013 |
| CN | 103381101 A | 11/2013 |
| CN | 103582460 A | 2/2014 |
| CN | 103607964 A | 2/2014 |
| DE | 102008028308 A1 | 4/2009 |
| EP | 0820726 A2 | 1/1998 |
| EP | 00996372 A1 | 5/2000 |
| EP | 1269935 A2 | 1/2003 |
| EP | 1527753 A2 | 5/2005 |
| EP | 1951129 A2 | 8/2008 |
| EP | 2326259 A1 | 6/2011 |
| EP | 2451363 A2 | 5/2012 |
| EP | 2713904 A1 | 4/2014 |
| EP | 2713905 A1 | 4/2014 |
| HK | 1134421 A1 | 3/2014 |
| JP | 2001286478 A | 10/2001 |
| JP | 2002516705 A | 6/2002 |
| JP | 2003512129 A | 4/2003 |
| JP | 2005522266 A | 7/2005 |
| JP | 2009512515 A | 3/2009 |
| JP | 2013226419 A | 11/2013 |
| KR | 20080081899 A | 9/2008 |
| WO | WO-9724978 A1 | 7/1997 |
| WO | WO-9726939 A1 | 7/1997 |
| WO | WO-9731672 A1 | 9/1997 |
| WO | WO-9823227 A1 | 6/1998 |
| WO | WO-9850102 A1 | 11/1998 |
| WO | WO-9905977 A1 | 2/1999 |
| WO | WO-9907294 A1 | 2/1999 |
| WO | WO-9915225 A1 | 4/1999 |
| WO | WO-0013593 A1 | 3/2000 |
| WO | WO-0130266 A1 | 5/2001 |
| WO | WO-0193782 | 12/2001 |
| WO | WO-0200139 | 1/2002 |
| WO | WO-0213899 A1 | 2/2002 |
| WO | WO-02071977 | 9/2002 |
| WO | WO-02078777 | 10/2002 |
| WO | WO-02087690 | 11/2002 |
| WO | WO-03059176 A2 | 7/2003 |
| WO | WO-03075793 A1 | 9/2003 |
| WO | WO-2004019790 A1 | 3/2004 |
| WO | WO-2004026149 A1 | 4/2004 |
| WO | WO-2004105599 A1 | 12/2004 |
| WO | WO-2005033409 A1 | 4/2005 |
| WO | WO-2005082279 A1 | 9/2005 |
| WO | WO-2006119422 A2 | 11/2006 |
| WO | WO-2007/047851 A2 | 4/2007 |
| WO | WO-2008/151204 A1 | 12/2008 |
| WO | WO-2010/028314 A1 | 3/2010 |
| WO | WO-2011029063 A2 | 3/2011 |
| WO | WO-2012167137 A1 | 12/2012 |
| WO | WO-2012167150 A1 | 12/2012 |
| WO | WO-2012167156 A1 | 12/2012 |
| WO | WO-2013169380 A1 | 11/2013 |
| WO | WO-2014029835 A1 | 2/2014 |
| WO | WO-2015179377 A1 | 11/2015 |

OTHER PUBLICATIONS

International Search Report for International Application No. PCT/US06/40907, Mail Date May 1, 2008, 2 pages.
Extended European Search Report, European Application No. 06826291.4, Nov. 19, 2009, 7 pages.
Singapore Examination Report for Singapore Application No. 200802811-0, Mail Date Jul. 12, 2009, 7 pages.
International Search Report and Written Opinion for International Application No. PCT/US2009/056133, Mail Date Oct. 26, 2009, 11 pages.
Micrus Copr.; "Concurse 14 Microcatheter" Product Brochure; Sunnyvale ,CA, USA.
Cordis NeuroVascular, Inc.; "Masstransit Microcatheter," Product Brochure; No. 153-8383-3; Miami Lakes, FL, USA (2003).
Cordis NeuroVascular, Inc.; "Prolwer Select Plus Microcatheter," Product Brochure; No. 154-9877-1; Miami Lakes, FL, USA (2003).
Cordis NeuroVascular, Inc.; "Rapid Transit Microcatheter," Product Brochure; No. 152-7369-2; Miami Lakes, FL, USA (2003).
Cordis NeuroVascular, Inc.; "Prowler Select LP Microcatheter," Product Brochure; No. 155-5585; Miami Lakes, FL, USA (2004).
Gupta et al. SMST-2003: Proc. Intl. Conf. Shape Memory Superelastic Technol.; Pacific Grove, CA; p. 639; 2003.
International Search Report and Written Opinion for Application No. PCT/US2010/047908, Mail Date May 25, 2011.
International Search Report and Written Opinion for International Application No. PCT/US2010/047908, mailing date Mar. 15, 2012, 11 pages.
International Search Report and Written Opinion for International Application PCT/US2012/040536, mailing date Oct. 15, 2012, 17 pages.
International Search Report and Written Opinion for International Application No. PCT/US2012/040552, mailing date Aug. 28, 2012, 14 pages.
International Search Report and Written Opinion for International Application PCT/US2012/040558, mailing date Oct. 8,2012, 17 pages.
International Search Report and Written Opinion for International Application PCT/US2012/059133, mailing date Mar. 11, 2013,15 pages.
International Search Report and Written Opinion for International Application PCT/US2013/031793, mailing date Jun. 26, 2013, 14 pages.

* cited by examiner

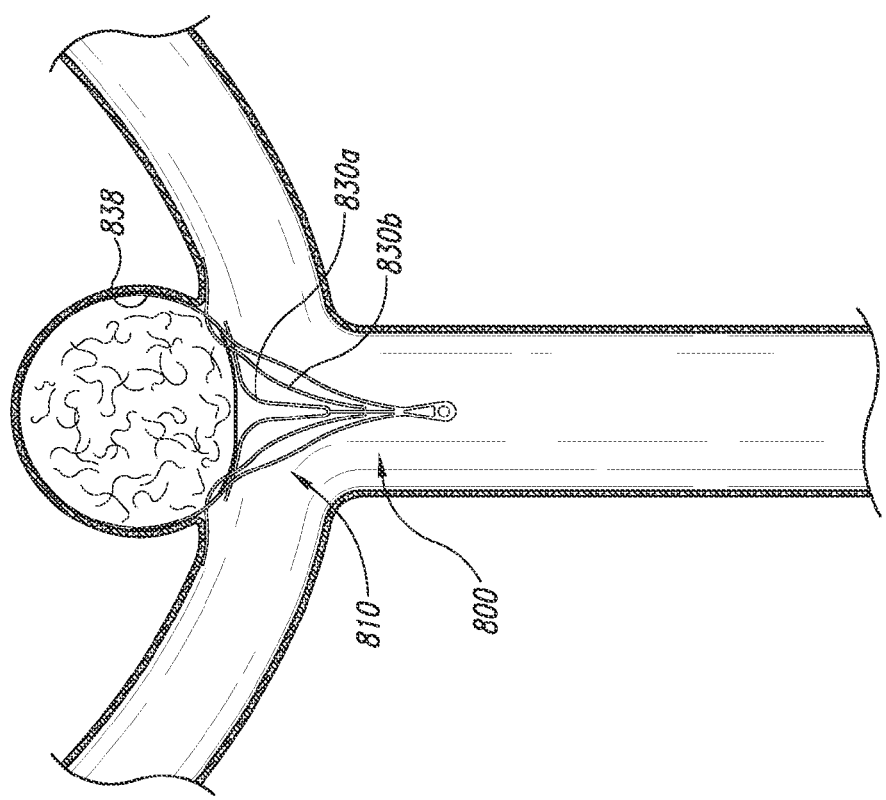
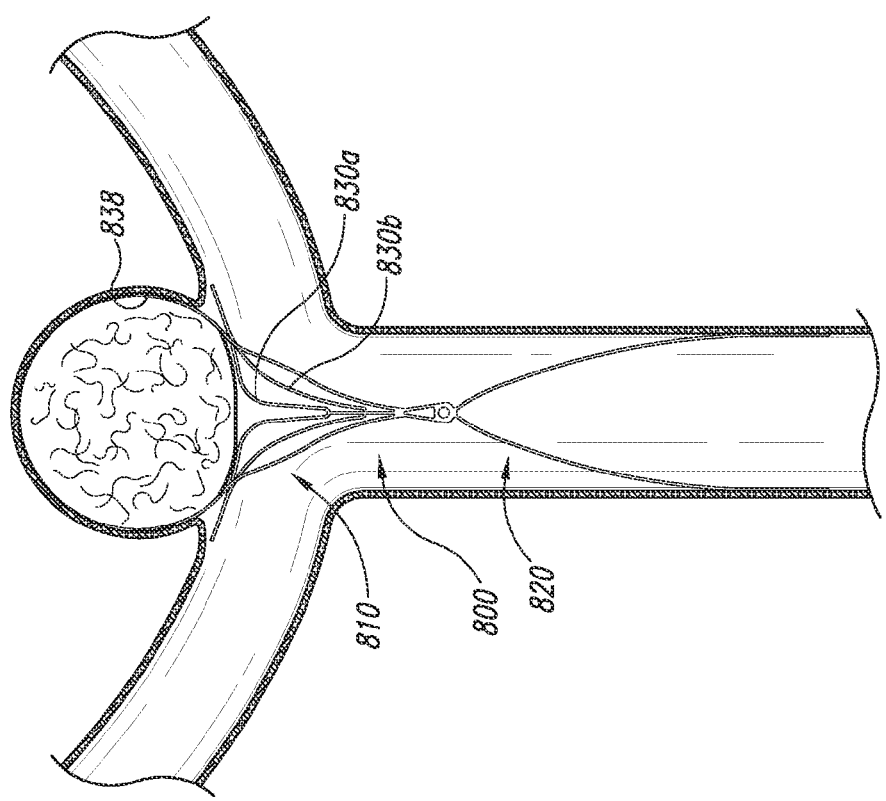

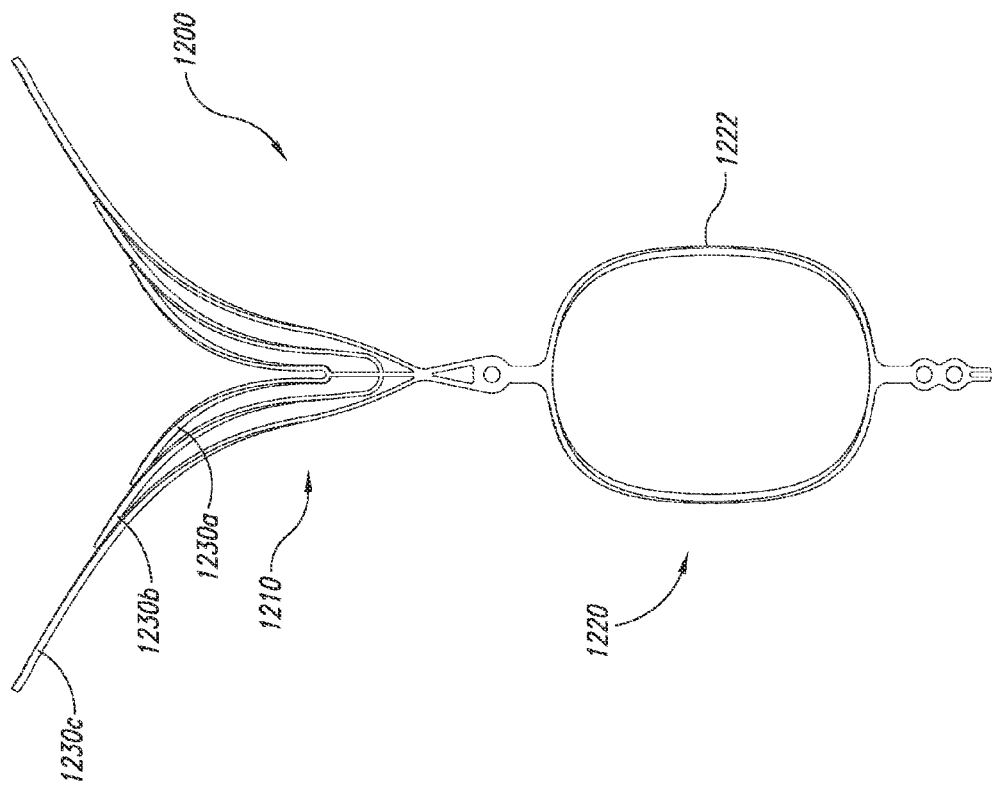
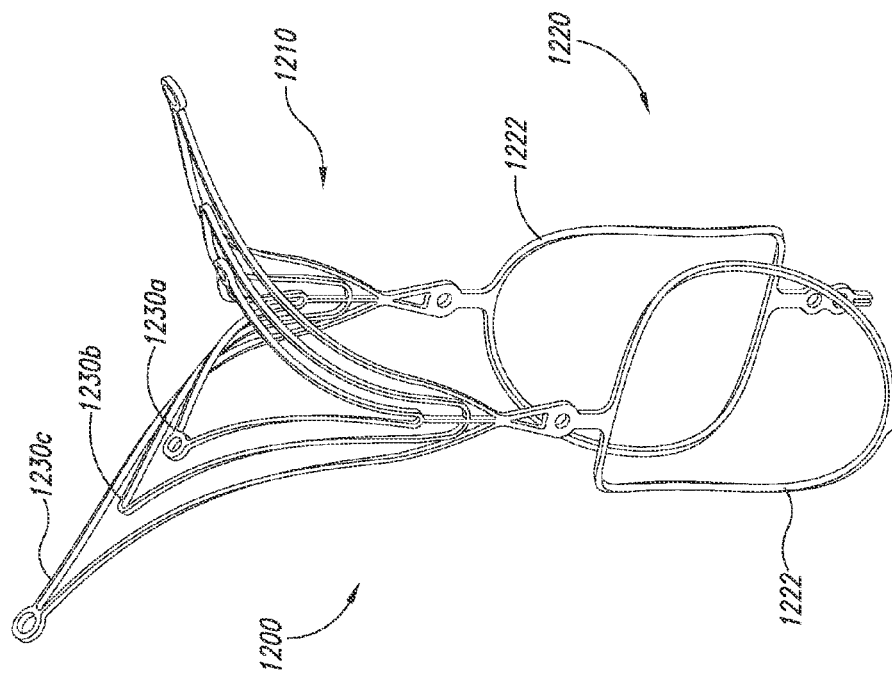
Fig. 12A
Fig. 12B

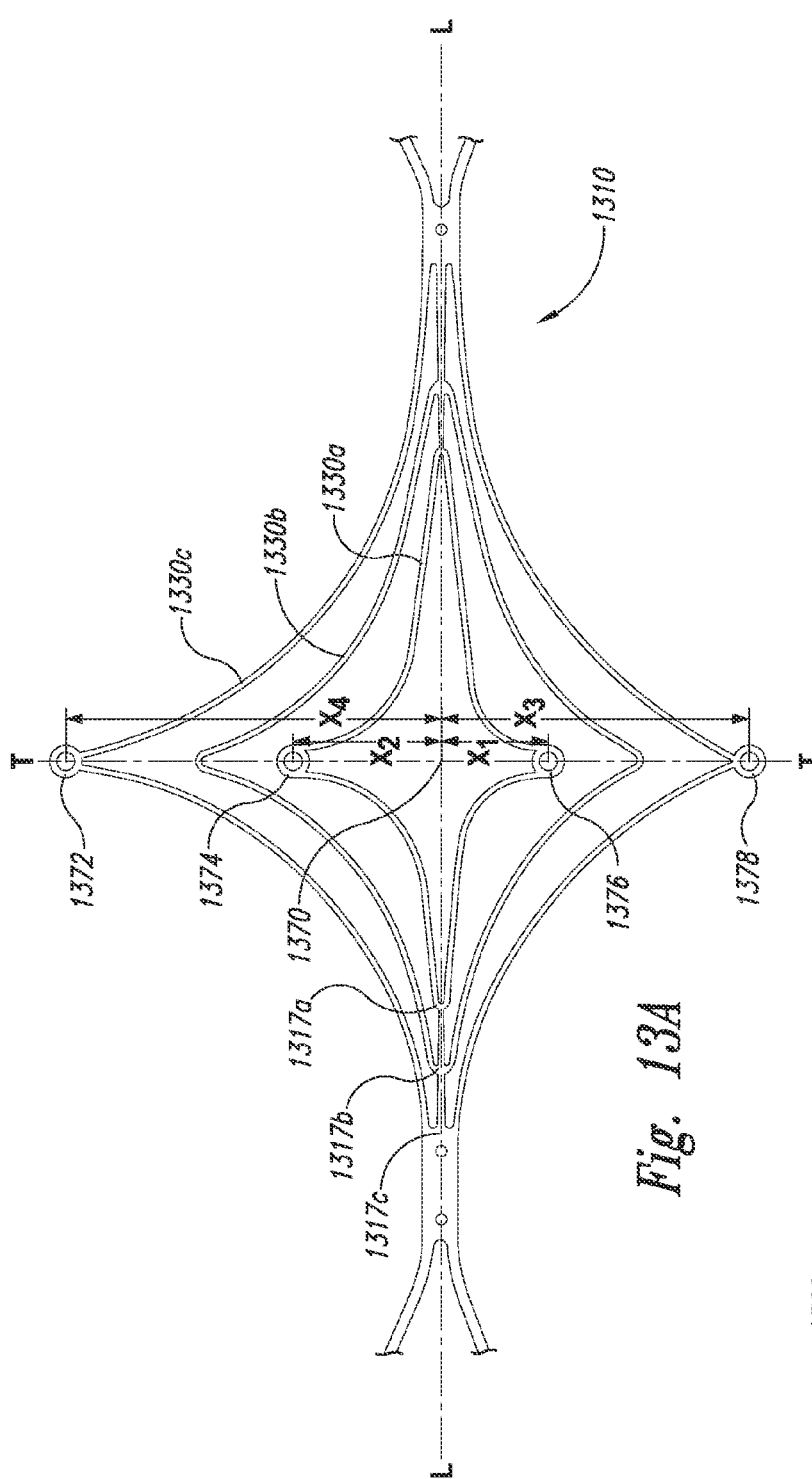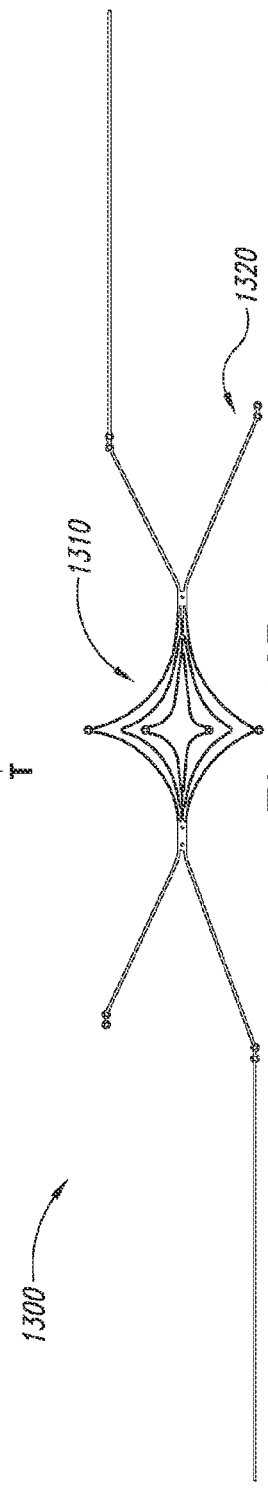

DEVICES, SYSTEMS AND METHODS FOR ENCLOSING AN ANATOMICAL OPENING

CROSS-REFERENCE TO RELATED APPLICATIONS

This application is a divisional of U.S. patent application No. 13/646,602, now U.S. Pat. No. 9,119,625, filed on Oct. 5, 2012 and entitled DEVICES, SYSTEMS AND METHODS FOR ENCLOSING AN ANATOMICAL OPENING, which claims the benefit of U.S. Provisional Application No. 61/543,785, filed on Oct. 5, 2011 and entitled DEVICES, SYSTEMS AND METHODS FOR ENCLOSING AN ANATOMICAL OPENING, all of which are incorporated herein by reference in their entireties.

TECHNICAL FIELD

The present technology relates to implantable therapeutic devices and methods for endovascular placement of devices at a target site, such as an opening at a neck of an aneurysm.

BACKGROUND

Many of the currently available surgical approaches for closing openings and repairing defects in anatomical lumens and tissues (e.g., blood vessels), septal defects, and other types of anatomical irregularities and defects are highly invasive. Surgical methods for clipping brain aneurysms, for example, require opening the skull, cutting or removing overlying brain tissue, clipping and repairing the aneurysm from outside the blood vessel, and then reassembling tissue and closing the skull. Surgical techniques for repairing septal defects are also highly invasive. The risks related to anesthesia, bleeding, and infection associated with these types of procedures are high, and tissue that is affected during the procedure may or may not survive and continue functioning.

Minimally invasive surgical techniques have been developed to place occlusive devices within or across an opening or cavity in the body, such as in the vasculature, spinal column, fallopian tubes, bile ducts, bronchial and other air passageways, and the like. In general, an implantable device is guided along a delivery catheter and through a distal opening of the catheter using a pusher or delivery wire to deploy the device at a target site in the vasculature. Once the occlusive device has been deployed at the target site, it is detached from the pusher mechanism without disturbing placement of the occlusive device or damaging surrounding structures.

Minimally invasive techniques are also highly desirable for treating aneurysms. In general, the minimally invasive therapeutic objective is to prevent material that collects or forms in the cavity from entering the bloodstream and to prevent blood from entering and collecting in the aneurysm. This is often accomplished by introducing various materials and devices into the aneurysm. One class of embolic agents includes injectable fluids or suspensions, such as microfibrillar collagen, various polymeric beads, and polyvinylalcohol foam. Polymeric agents may also be cross-linked to extend their stability at the vascular site. These agents are typically deposited at a target site in the vasculature using a catheter to form a solid space-filling mass. Although some of these agents provide for excellent short-term occlusion, many are thought to allow vessel recanalization due to their absorption into the blood. Other materials, such as hog hair and suspensions of metal particles, have also been proposed and used to promote occlusion of aneurysms. Polymer resins, such as cyanoacrylates, are also employed as injectable vaso-occlusive materials. These resins are typically mixed with a radiopaque contrast material or are made radiopaque by the addition of a tantalum powder. Accurate and timely placement of these mixtures is crucial and very difficult because it is difficult or impossible to control them once they have been placed in the blood flow.

Implantable vaso-occlusive metallic structures are also well known and commonly used. Many conventional vaso-occlusive devices have helical coils constructed from a shape memory material or noble metal that forms a desired coil configuration upon exiting the distal end of a delivery catheter. The function of the coil is to fill the space formed by an anatomical defect and to facilitate the formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

Techniques for delivering conventional metallic vaso-occlusive devices to a target site generally involve a delivery catheter and a detachment mechanism that detaches the devices, such as a coil, from a delivery mechanism after placement at the target site. For example, a microcatheter can be initially steered through the delivery catheter into or adjacent to the entrance of an aneurysm either with or without a steerable guidewire. If a guidewire is used, it is then withdrawn from the microcatheter lumen and replaced by the implantable vaso-occlusive coil. The vaso-occlusive coil is advanced through and out of the microcatheter and thus deposited within the aneurysm or other vessel abnormality. It is crucial to accurately implant such vaso-occlusive devices within the internal volume of a cavity and to maintain the device within the internal volume of the aneurysm. Migration or projection of a vaso-occlusive device from the cavity may interfere with blood flow or nearby physiological structures and poses a serious health risk.

In addition to the difficulties of delivering implantable occlusion devices, some types of aneurysms are challenging to treat because of structural features of the aneurysm or because of particularities of the site. Wide-neck aneurysms, for example, are known to present particular difficulty in the placement and retention of vaso-occlusive coils. Aneurysms at sites of vascular bifurcation are another example where the anatomical structure poses challenges to methods and devices that are effective in treating the typical sidewall aneurysms.

In view of such challenges, implanting conventional embolic coils, other structures, or materials in the internal space of an aneurysm has not been an entirely satisfactory surgical approach. The placement procedure may be arduous and lengthy because it often requires implanting multiple devices, such as coils, serially in the internal space of the aneurysm. Higher risks of complication from such sources as anesthesia, bleeding, thromboembolic events, procedural stroke, and infection are associated with such longer procedures. Moreover, because placement of structures in the internal space of an aneurysm does not generally completely occlude the opening, recanalization of the original aneurysm may occur, and debris and occlusive material may escape from within the aneurysm to create a risk of stroke or vessel blockage. Blood may also flow into the aneurysm and other blood vessel irregularities after the placement of embolic devices, which may increase the risks of complication and further enlargement of the aneurysm.

Despite the numerous conventional devices and systems available for implanting embolic materials in an aneurysm and for occluding physiological defects using minimally invasive techniques, these procedures remain risky and rarely restore the physiological structure to its normal, healthy condition. It is also challenging to position conventional implantable devices during deployment, prevent shifting or migration of such devices after deployment, and preserve blood flow in neighboring vessels following after deployment.

BRIEF DESCRIPTION OF THE DRAWINGS

FIGS. 8B and 8C are front views of the aneurysm device of FIG. 8A being placed at an aneurysm in accordance with embodiments of the technology.

FIGS. 12A and 12B are isometric and side views, respectively, of an aneurysm device configured in accordance with embodiments of the technology.

FIGS. 13A and 13B are top views an aneurysm device in an unassembled configuration in accordance with embodiments of the technology.

DETAILED DESCRIPTION

The present disclosure describes implantable therapeutic devices and methods for endovascular placement of devices at a target site, such as an opening at a neck of an aneurysm. In several embodiments, a therapeutic aneurysm device is endovascularly deliverable to a site proximate to an arterial aneurysm. The aneurysm device comprises a closure structure having a distal-facing aspect configured to at least partially occlude the aneurysm and a proximal-facing aspect configured to arch over lumina of an artery. The device further includes a supplemental stabilizer connected to the closure structure and configured to reside in the artery and press outward against a luminal wall thereof. In some embodiments, the device can also include a barrier spanning at least a portion of the distal-facing aspect of the closure structure and configured to further occlude a neck of the aneurysm.

The following description provides specific details for a thorough understanding of, and enabling description for, embodiments of the disclosure. Well-known structures, systems, and methods often associated with aneurysm treatment have not been shown or described in detail to avoid unnecessarily obscuring the description of the various embodiments of the disclosure. In addition, those of ordinary skill in the relevant art will understand that additional embodiments may be practiced without several of the details described below.

Figure 1A:
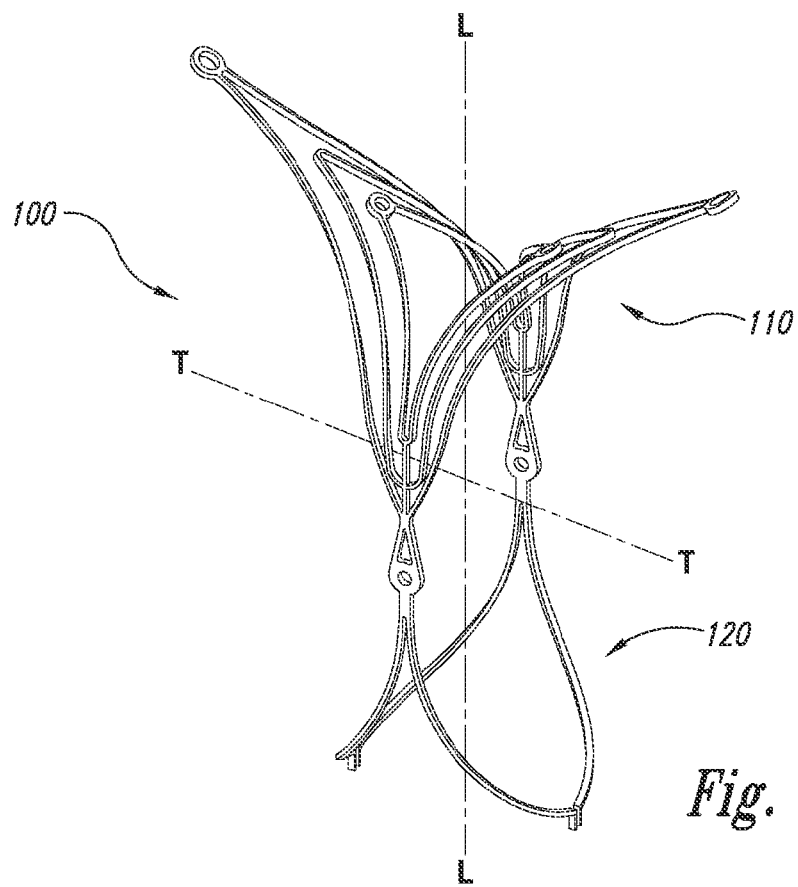
FIG. 1A is an isometric view of an aneurysm device configured in accordance with an embodiment of the technology.
Figure 1B:
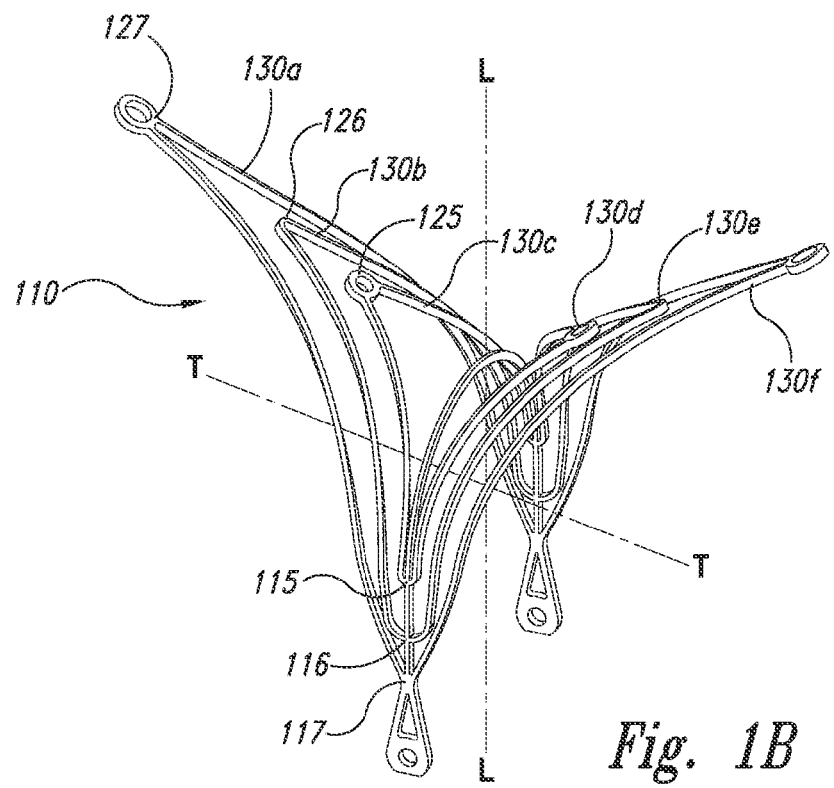
FIG. 1B is an isometric view of a closure structure portion of the aneurysm device of FIG. 1A.

FIG. 1A is an isometric view of an aneurysm device 100 having a closure structure 110 and a support or supplemental stabilizer 120 configured in accordance with embodiments of the technology. FIG. 1B is an isometric view of the closure structure 110. Referring to FIGS. 1A and 1B together, the closure structure 110 can be a frame, scaffold, or other structure that at least partially occludes the neck of an aneurysm to prevent embolic coils or other coagulative material within the aneurysm from escaping into the bloodstream. The closure structure 110 comprises a plurality of scaffold struts or supports 130 (identified individually as struts 130a-130f). The struts 130 are joined together at corners 115, 116, and 117. The corners 115, 116, and 117 can be longitudinal corners that define the proximal end of the closure structure 110 that extends along the longitudinal axis L-L. The struts 130 can further include lateral corners 125, 126, and 127 defining a lateral aspect of the closure structure 110 that extends along the lateral axis T-T. The embodiment of the closure structure 110 illustrated in FIGS. 1A and 1B is generally symmetrical with respect to the centerlines of both the longitudinal L-L and the lateral T-T axes, but in other embodiments the closure structure 110 may have an asymmetrical configuration with respect to either or both of the longitudinal and lateral axes. Although the corners 125, 126, and 127 are illustrated as being rounded or looped, other embodiments of the corners may have a more pointed profile, a more complex curve, or other angular configurations. The struts 130 may be formed integrally with one another from a sheet of material, or separate struts may be formed and bonded together at the corners.

The closure structure 110 can define a distal framework portion, and the supplemental stabilizer 120 can define a proximal framework portion. Each of these portions can have one or more pairs of struts 130 (e.g., strut 130a is "paired" with strut 130f). In some embodiments, the struts 130 can curve inwardly toward the longitudinal axis L-L of the aneurysm device 100. The outline of the struts 130 is typically that of a quadrilateral form. In some embodiments, the struts 130 can have a rhombus-like configuration or diamond shape. In several embodiments, the struts 130 can bend to provide a tailored fit to a particular vasculature. In some embodiments, the struts 130 can bend or flexibly move independently of one another. For example, strut 130c may bend further into an aneurysm body than strut 130b. This independent adjustability can provide a customized fit to the particular contours of a given aneurysm, creating a more secure hold.

As discussed above, the struts 130 can be symmetrical (e.g., the same length along orthogonal axes) or asymmetrical in which one side of the rhombus-like structure can have an axis longer than the other side. Although many closure structures 110 described below have quadrilateral forms, the closure structures 110 are not limited to these shapes in that the distal-facing aspect of the distal framework portion may have other shapes, such as polygons or polygonal curvilinear shapes. In several embodiments, the rhombus-like supports 130 are concentric with a center at the longitudinal axis L-L of the aneurysm device 100. The lateral apices of the closure structure 102 are disposed at opposing ends of the lateral axis T-T of the distal framework portion. The two portions of the distal framework portion opposite each other across the longitudinal axis L-L may define lateral leaves of the distal framework portion.

In various embodiments, the closure structure 110 can be used in combination with the supplemental stabilizer 120 or independently from the supplemental stabilizer 120 at a neck of an aneurysm. The laterally-extending branches of the closure structure 110 and the supplemental stabilizer 120 hold the curved portion of the closure structure 110 at the neck of the aneurysm. However, in some embodiments, using the closure structure 110 independently of the supplemental stabilizer 120 can decrease the amount of contact the aneurysm device 100 has with a patient's vasculature. For example, in some embodiments, the closure structure 110 can be used independently of the supplemental stabilizer in the treatment of a ruptured aneurysm. In some embodiments, the supplemental stabilizer 120 can be used during placement of the closure structure 110, but then removed.

Figure 1C:
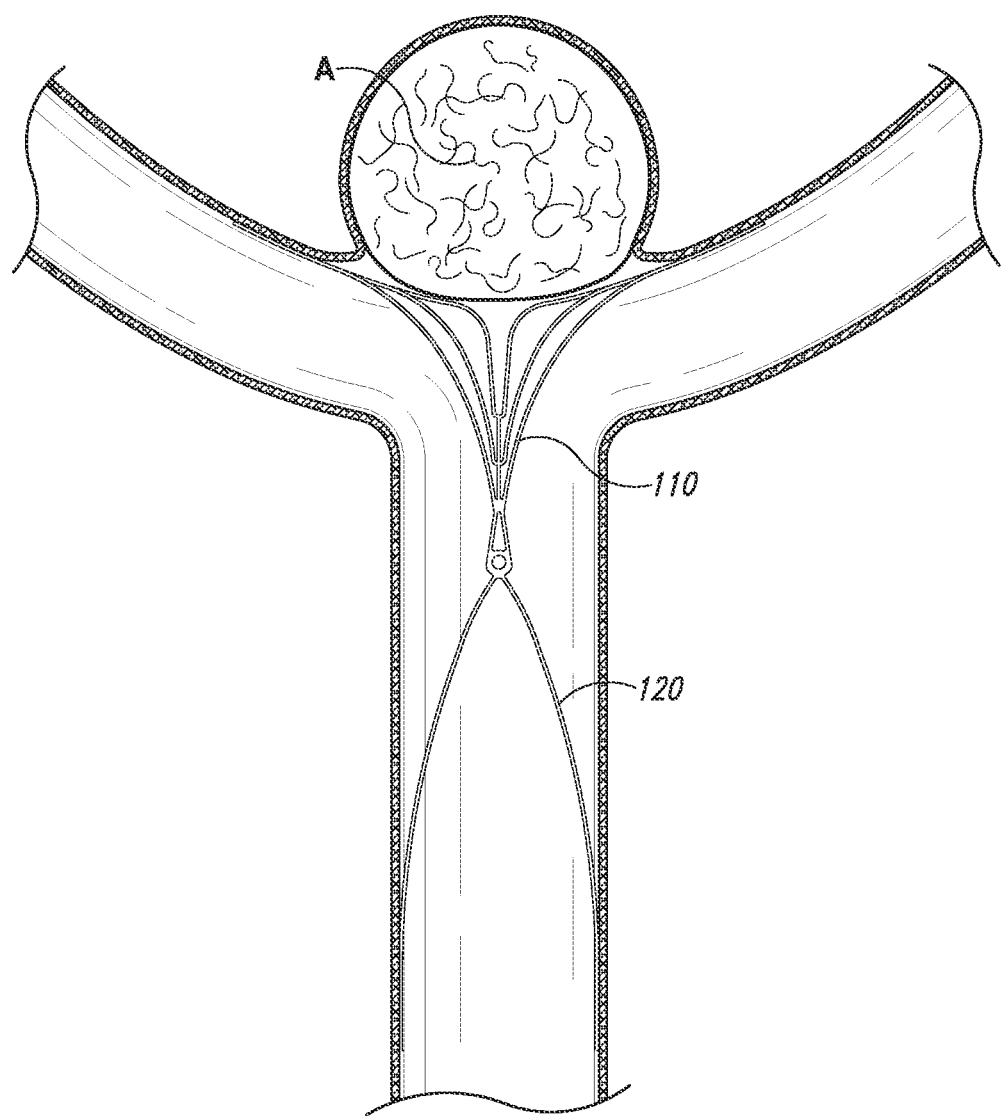
FIG. 1C is a front view of the aneurysm device of FIG. 1A implanted at an aneurysm and configured in accordance with embodiments of the technology.

FIG. 1C is a front view of the aneurysm device of FIG. 1A in a deployed configuration and implanted at an aneurysm in accordance with embodiments of the technology. In the deployed configuration, the closure structure 110 has a distally projecting arch defined by a curved section of the distal framework portion. The supplemental stabilizer 120 extends proximally from the closure structure 110 at an angle relative to a lateral axis. A proximal-facing aspect of the arch of the closure structure 110 extends over the lumina of the bifurcating arteries. A distal-facing aspect of the arch of the closure structure 110 generally presses against the luminal surfaces of the bifurcating arteries. The distal-facing aspect of the closure structure 110 is configured to substantially align with or otherwise conform to the neck of the aneurysm by forming a curved surface that compatibly aligns with or engages the neck and the surrounding wall of the side branch vessels. In some embodiments, the distal-facing aspect has a complex curve, such as a hyperbolic paraboloid (e.g., a generally saddle-shaped form). In the illustrated embodiment, the hyperbolic paraboloid comprises a generally Y-shaped curve with a depressed central portion. The supplemental stabilizer 120 can have struts that extend down into the parent artery and press outwardly against the luminal surface thereof.

The distal-facing aspect or back of the proximal-facing surface generally aligns against the luminal surfaces of the bifurcating arteries, the sides of the arch extending down into the parent artery and aligned against the luminal surface thereof. The proximal face of the arch is generally and substantially transverse (perpendicular or orthogonal) to the lateral axis of the proximal framework. The arch spans unobtrusively over the lumina of the bifurcating arteries, forming no incursion into the vascular flow path. More particularly, the arch can be a non-enclosed opening or hole, but instead a structure entirely open in the proximal direction. In further embodiments, as will be discussed in more detail below, the closure structure 110 can include a cover or barrier portion spanning across one or more distal framework struts and configured to occlude the neck of the aneurysm.

Figure 2:
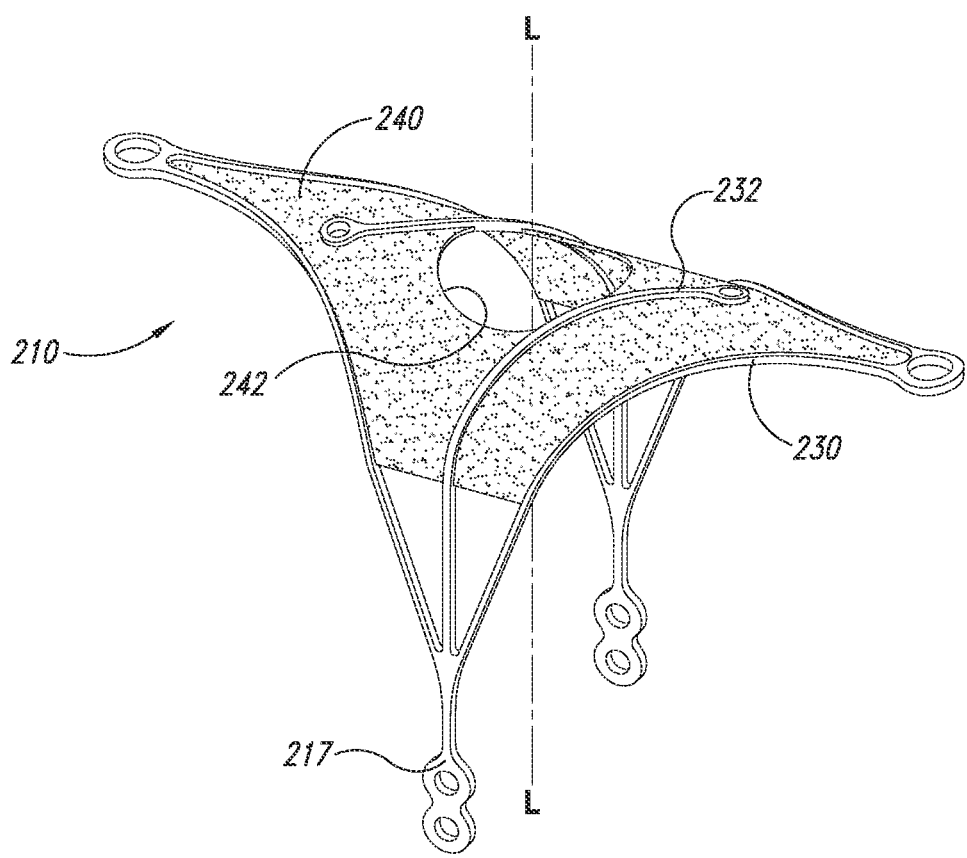
FIG. 2 is an isometric view of a closure structure portion of an aneurysm device configured in accordance with embodiments of the technology.

FIG. 2 is an isometric view of a closure structure 210 of an aneurysm device configured in accordance with embodiments of the technology. The closure structure 210 has several features generally similar to the closure structure 110 described above with reference to FIGS. 1A-1C. The closure structure 210 further includes a barrier 240 spanning across a distal-facing aspect.

In the illustrated embodiment, the closure structure 210 includes perimeter struts 232 and curved inner arms 230 that meet the perimeter struts 232 at longitudinal corner points 217. The closure structure 210 is capable of temporary or permanent attachment to a supplemental stabilizer (such as the supplemental stabilizer 120 described above with reference to FIG. 1A) at the corner points 217. The inner arms 232 extend distally from the corner point 217, along a longitudinal midline L-L of the closure structure 210, and curve distally and laterally to an off-centered position. The inner arms 232 therefore allow the closure structure 210 and the barrier 240 to keep and maintain a shape in a deployed configuration and to fold up or compress in a spiral manner during delivery and/or removal.

The barrier 240 can be formed with or permanently or removably attached to the perimeter and inner arms 232, 230. The barrier 240 can comprise one or more permeable or semi-permeable membranes, covers, sheets, panels, mesh, or other structures that form an occlusive or semi-occlusive covering that (a) restricts, diverts, redirects, or inhibits vascular flow into the cavity of the aneurysm and/or (b) prevents materials from escaping the cavity. In this aspect, devices and methods of the described technology may provide repair and reconstruction of a blood vessel or a junction of blood vessels by placement and retention of the closure structure 210 across the neck of the aneurysm that diverts blood flow away from the aneurysm. Following placement and deployment, the barrier 240 may substantially cover the aneurysm neck and the closure structure 210 can form a structure that substantially conforms to the tissue surrounding the aneurysm and/or the neighboring vessel walls. The highly conforming fit generally restores the vascular anatomical neighborhood to a normal or more normal configuration, thereby supporting a normal vascular flow pattern and overall function. In the illustrated embodiments, the barrier 240 includes a barrier aperture 242 configured to provide access to the aneurysm (e.g., access for a catheter, access to deliver coils, etc.) As will be described in further detail below, the barrier 240 can comprise a single sheet or panel, or can comprise a plurality of sheets or panels layered and/or otherwise arranged on the device to achieve a desired barrier pattern and/or structure.

Figure 3:
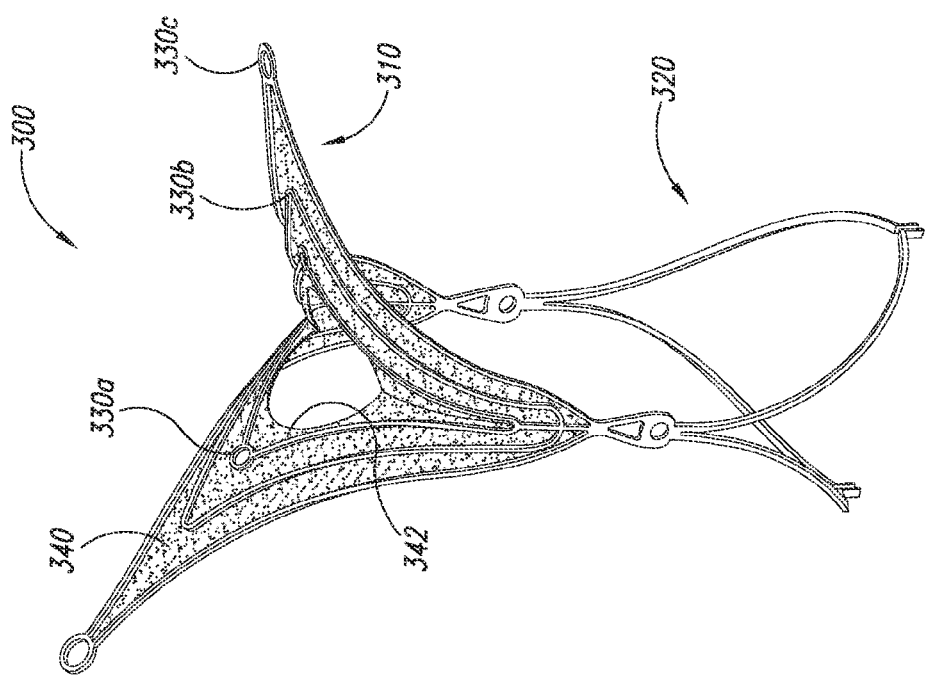
FIG. 3 is an isometric view of an aneurysm device configured in accordance with embodiments of the technology.

FIG. 3 is an isometric view of an aneurysm device 300 configured in accordance with embodiments of the technology. Generally similar to the aneurysm devices described above, the aneurysm device 300 includes a closure structure 310 and a supplemental stabilizer 320. The closure structure 310 comprises a plurality of nested, rhombus-shaped pairs of struts 330a-330c (collectively struts, 330). A barrier 340 spans the struts 330 and includes a central hole or slit 342 at a central portion of the closure structure 310, within the innermost set of struts 330a.

Figure 4:
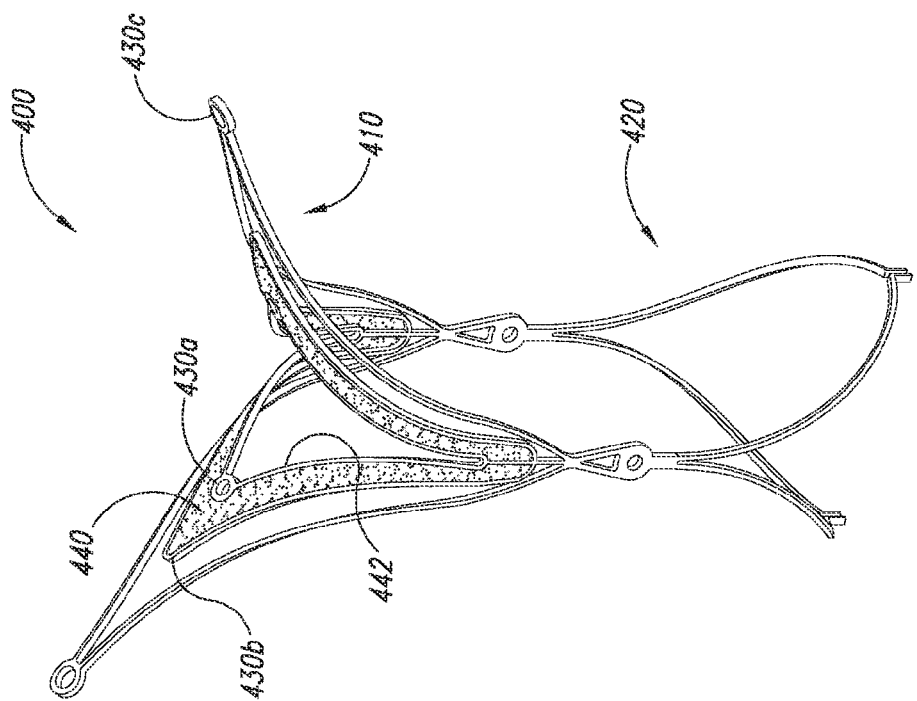
FIG. 4 is an isometric view of an aneurysm device configured in accordance with embodiments of the technology.

FIG. 4 is an isometric view of an aneurysm device 400 configured in accordance with embodiments of the technology. Generally similar to the aneurysm device 300 described above with reference to FIG. 3, the aneurysm device 400 includes a closure structure 410 and a supplemental stabilizer 420. The closure structure 410 comprises a plurality struts 430a-430c (collectively struts, 430) forming nested rhombus shapes. In this embodiment, however, a barrier 440 spans only the space between the innermost struts 330a and the middle struts 330b.

The illustrated configurations are merely representative of the numerous arrangements the struts 430 and barrier 440 could take. For example, there could be more or fewer than three sets of nested struts 430, and the barrier 440 could cover more or fewer areas or parts of areas between the struts 430. In some embodiments, the degree of barrier coverage across the struts can be selected based on a desired degree of occlusion, type or characteristics of the aneurysm, and/or desired access to the body of the aneurysm.

Figure 5:
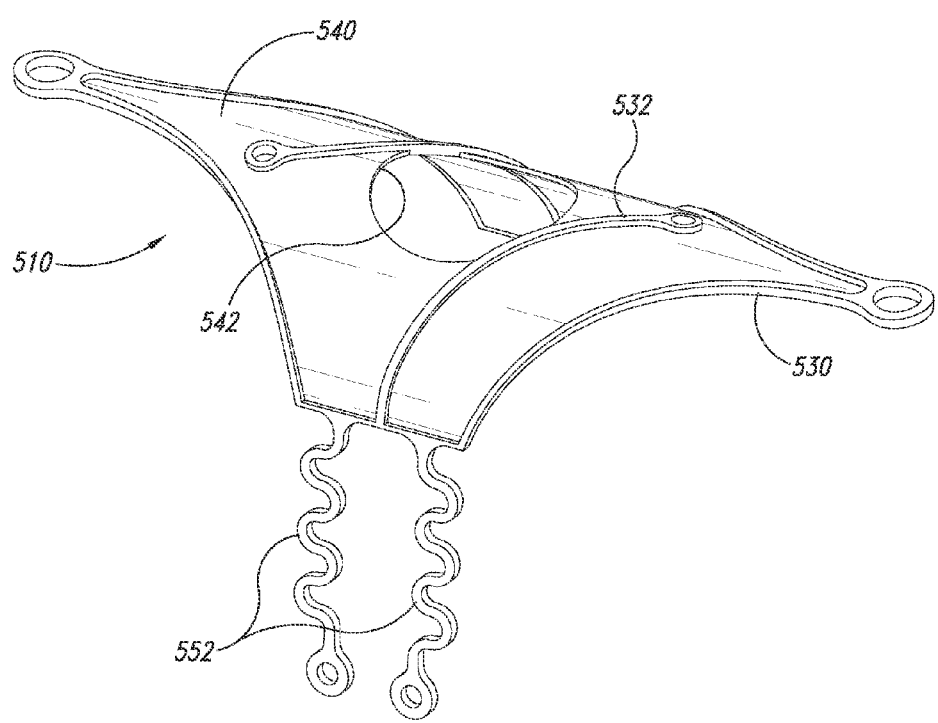
FIG. 5 is an isometric view of a closure structure portion of an aneurysm device configured in accordance with embodiments of the technology.

FIG. 5 is an isometric view of a closure structure portion 510 of an aneurysm device configured in accordance with embodiments of the technology. The closure structure 510 has several features generally similar to the closure structure 210 described above with reference to FIG. 2. For example, the closure structure 510 has a barrier 540 spanning across perimeter struts 532 and curved inner arms 530. the barrier 540 includes an optional access aperture 542.

The closure structure 510 further includes flexible anchor legs 552 distally coupled to the perimeter struts 530. While two legs 552 are shown descending from the illustrated side of the closure structure 510, there can be more or fewer legs 552, of the same or different dimensions, in further embodiments of the technology. The anchor legs 552 can provide pivotable movement (or shock absorption) between the closure structure 610 and a supplemental stabilizer, such as the supplemental stabilizer 120 described above with reference to FIG. 1A. The anchor legs 552 can comprise springs, hinges, or other movable or flexible structures that would allow movement of the closure structure 510 relative to a supplemental stabilizer.

Figure 6A:
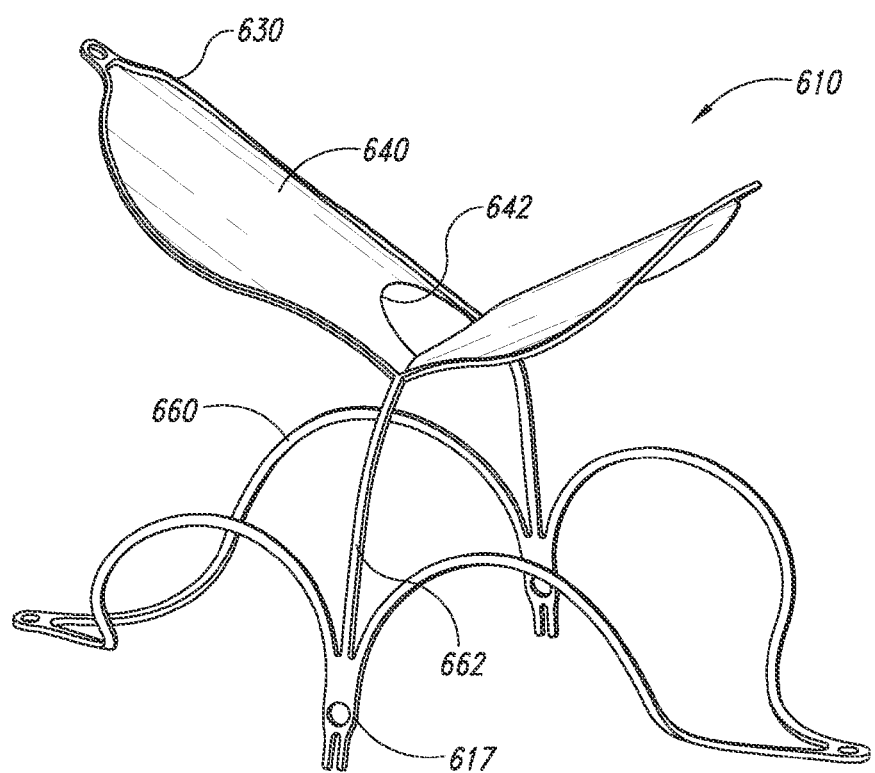
FIGS. 6A and 6B are isometric and front views, respectively, of a closure structure portion of an aneurysm device configured in accordance with embodiments of the technology.
Figure 6B:
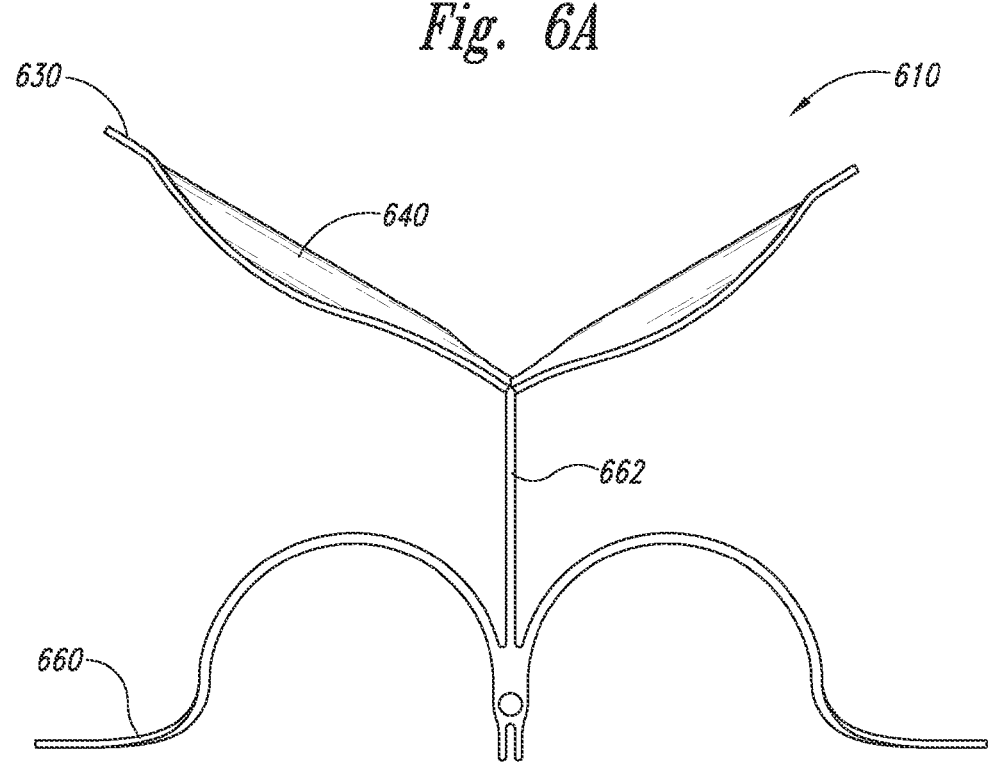
Figure 6C:
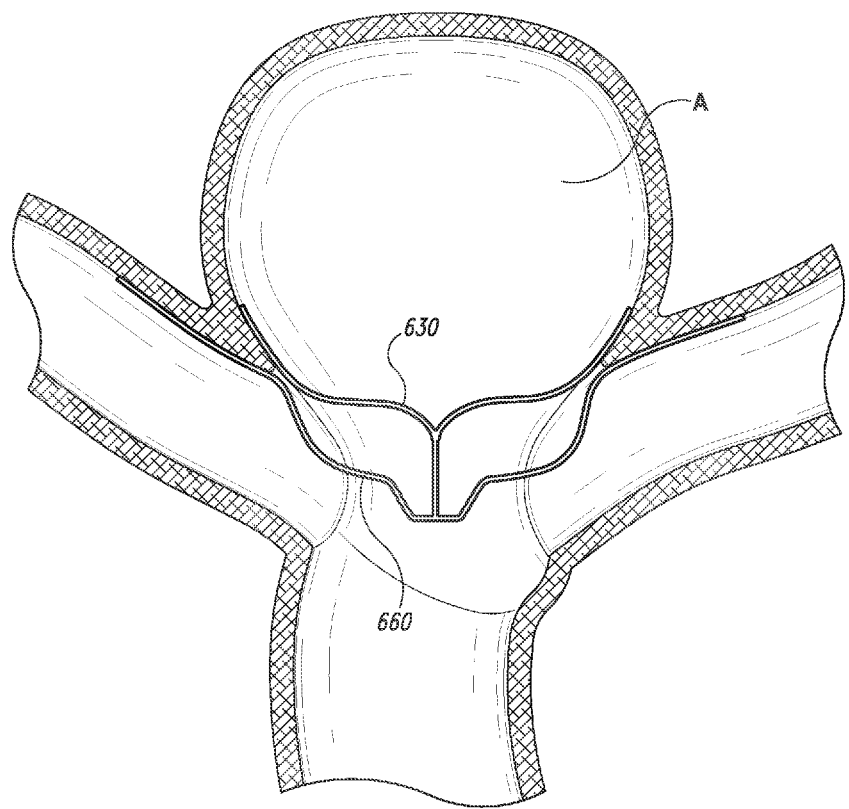
FIG. 6C is a front view of the closure structure portion of FIGS. 6A and 6B implanted at an aneurysm in accordance with embodiments of the technology.

FIGS. 6A and 6B are isometric and front views, respectively, of a closure structure 610 having several features generally similar to the closure structures described above. FIG. 6C is a front view of the closure structure 610 at an aneurysm in accordance with embodiments of the technology. Referring to FIGS. 6A-6C together, the closure structure 610 includes a barrier 640 spanning distal arms 630. The closure structure 610 further includes proximal arms 660 coupled to the distal arms 630 via a midline strut 662. In the illustrated embodiment, the midline strut 662 extends distally from a distal arm junction point 617. The barrier 640 can include an aperture 642 therein.

In several embodiments, at least one of the distal arms 630 or proximal arms 660 are curved or parabolic shaped to better conform to the shape of the aneurysm or the vasculature to provide the desired degree of aneurysm occlusion and device stability. For example, in the illustrated embodiment, the distal arms 630 extend distally but have a lateral, proximally-dipping curve, while the proximal arms 660 have an approximately 180-degree distal curve before projecting laterally. As best shown in FIG. 6C, the distal arms 630 can be placed within the aneurysm and can conform against the aneurysm wall, while the proximal arms 660 can conform against the luminal wall outside of the aneurysm.

Figure 7A:
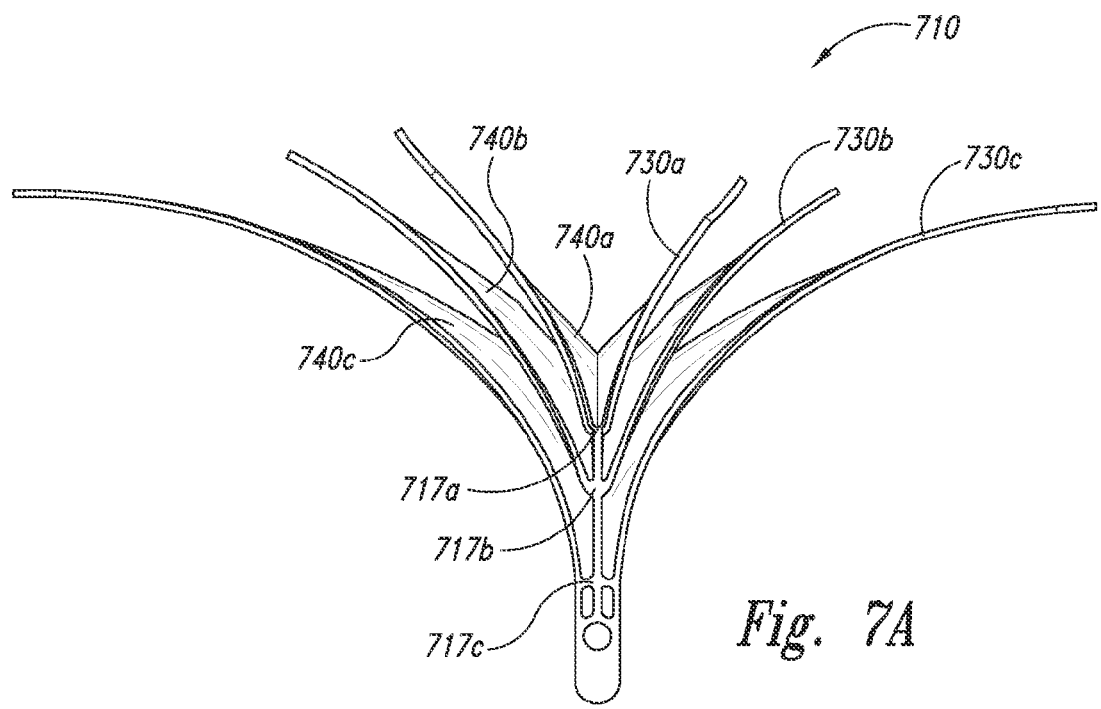
FIG. 7A is a front view of a closure structure portion of an aneurysm device configured in accordance with embodiments of the technology.
Figure 7B:
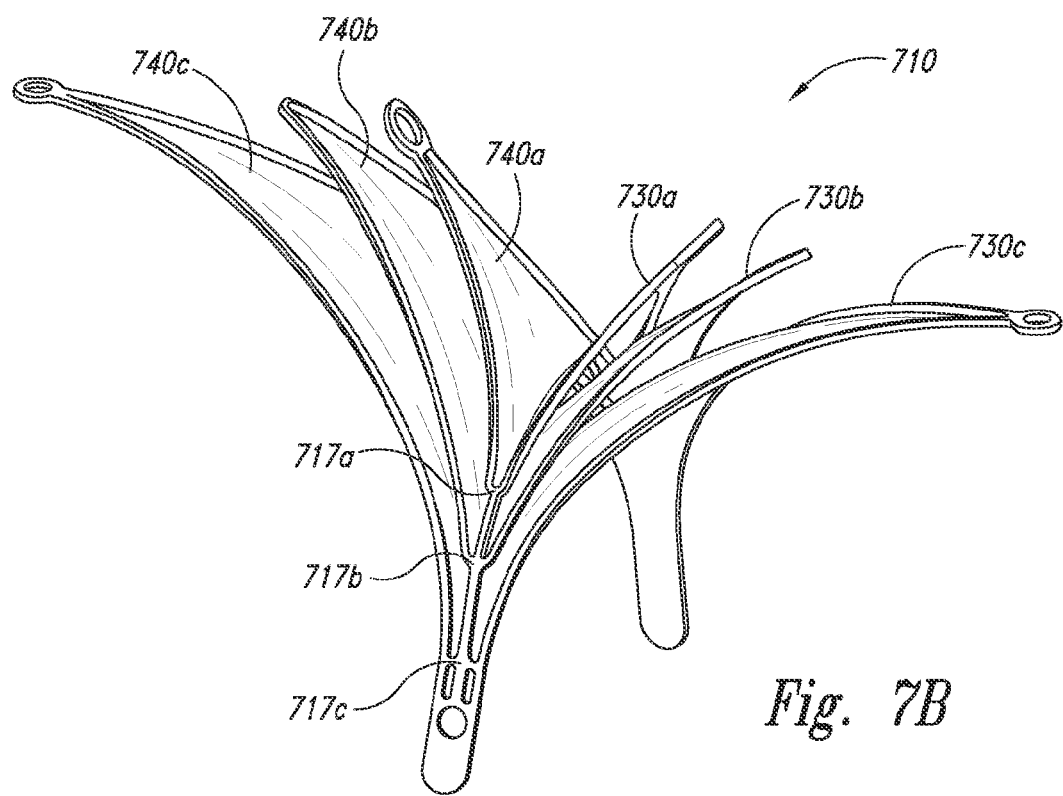
FIGS. 7B-7D are isometric views of the closure structure portion of FIG. 7A configured in accordance with embodiments of the technology.
Figure 7C:
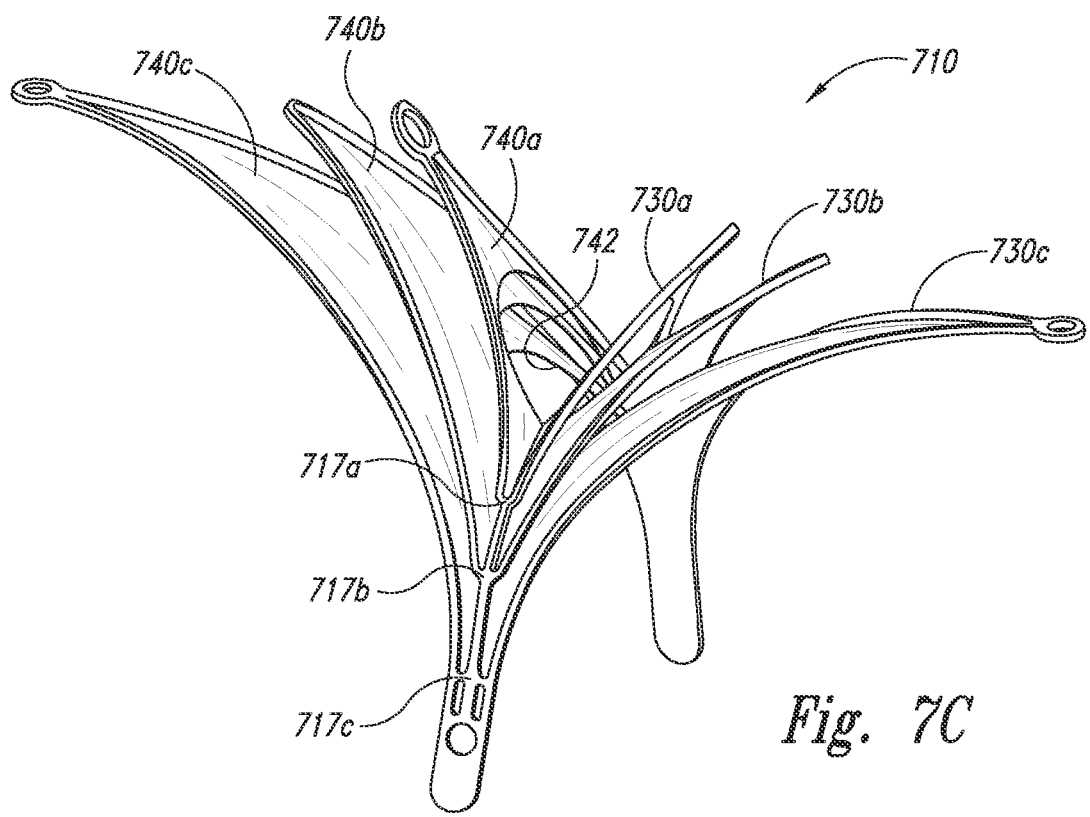
Figure 7D:
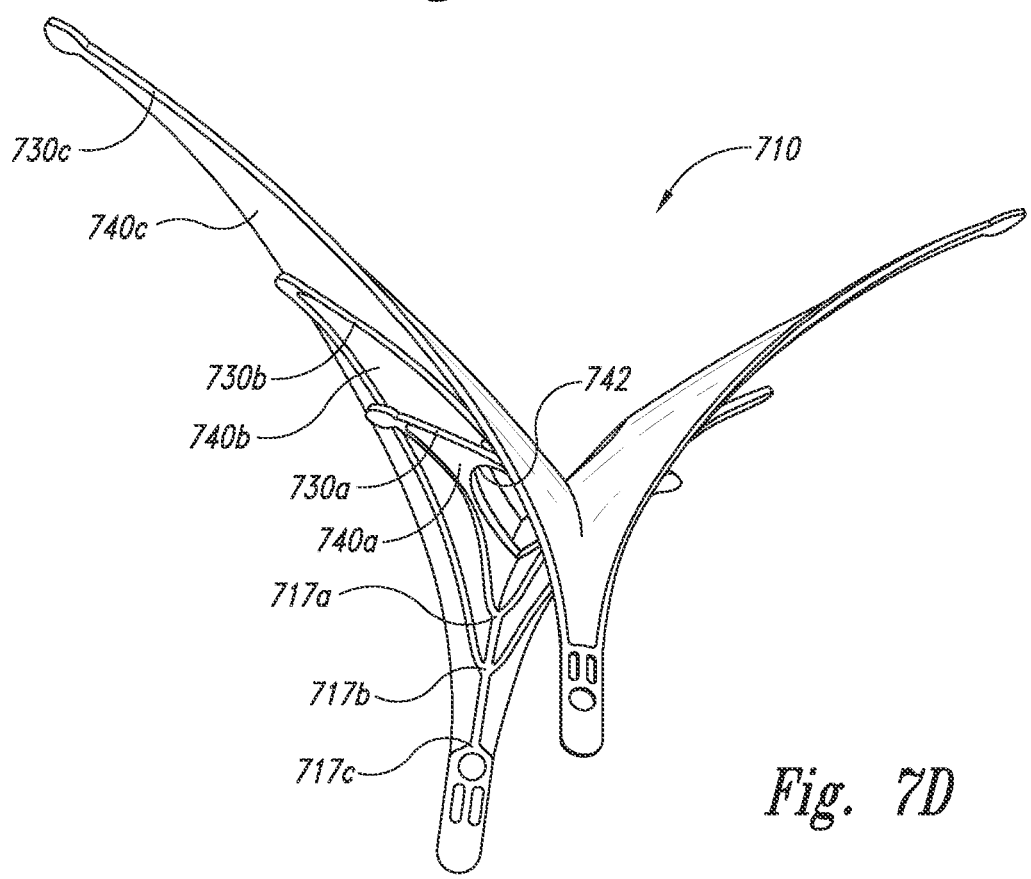

FIG. 7A is a front view of a closure structure 710 configured in accordance with embodiments of the technology. FIGS. 7B-7D are isometric views of the closure structure 710. Referring to FIGS. 7A to 7D together, the closure structure 710 includes multiple sets of nested, generally triangular-shaped baffles or panels 730a-730c (collectively panels 730). Each panel 730 comprises a strut framework and sheets or panels of barrier 740a-740c (collectively barrier 740). Pairs of panels 730 join at junctions 717a-717c on a central stem.

The panels 730 can be individually covered by the barrier 740, or pairs of struts (e.g., forming a V-shape) can be covered. One or more panels 730 can include an opening or hole 742. For example, in the illustrated embodiment, the closure structure 710 includes a central hole 742 that extends longitudinally through each pair of adjacent panels 730, thereby providing access from a proximal side of the closure structure 710 to the interior of the aneurysm. While the panels 730 are discussed as triangles, in further embodiments the panels 730 can be shaped as rectangles, circles, squares, or other polygonal or curved shapes. The panels 730 can laterally overlap and can be used to control, contain, and/or divert flow. The panels 730 can function as baffles that can pivotably bend or otherwise move relative to one another to adjust from an open state to a closed state. In various embodiments of use, one or more of the panels 730 can be inside the aneurysm while other panels 730 can be outside the aneurysm. In further embodiments, all of the panels 730 can be inside or outside the aneurysm.

Figure 8A:
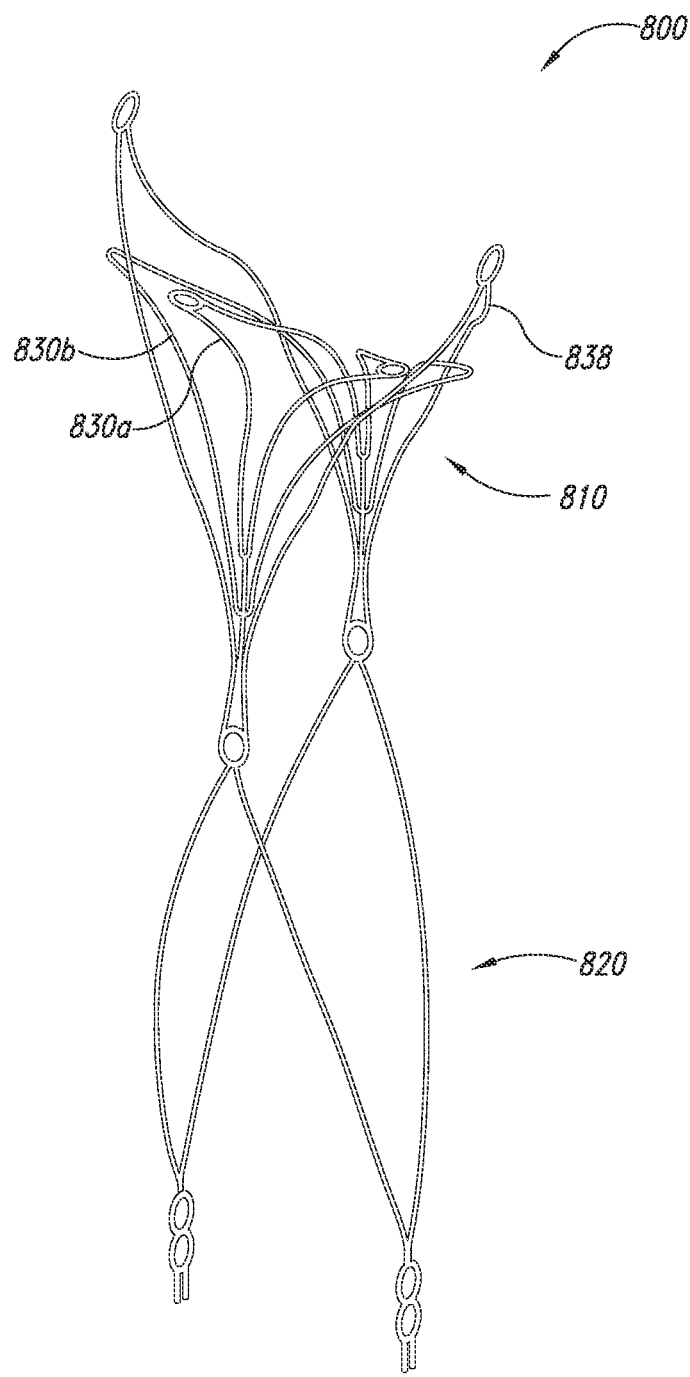
FIG. 8A is an isometric view of an aneurysm device configured in accordance with embodiments of the technology.

FIG. 8A is an isometric view of an aneurysm device 800 configured in accordance with embodiments of the technology. The aneurysm device 800 includes a closure structure 810 and a supplemental stabilizer 820. The closure structure 810 includes one or more rhombus-shaped sets of struts 830a, 830b (collectively struts 830), generally similar to the closure structures described above. The closure structure 810 further includes distally-extending anchor arms 838. In the illustrated embodiment, the struts 830 are curved distally and laterally, in some embodiments extending laterally beyond the anchor arms 838.

FIGS. 8B and 8C are front views of the aneurysm device of FIG. 8A being placed at an aneurysm in accordance with embodiments of the technology. The struts 830 are configured to curve against the exterior neck of the aneurysm. In further embodiments, one or more of the struts 830 can be placed within the aneurysm. The anchor struts 838 can be located within the side walls of the aneurysm and can provide improved fit/conformability to the aneurysm neck. As shown in FIG. 8C, in some embodiments, the supplemental stabilizer 820 can be removed upon stable placement of the closure structure 810 or can be not used at all.

Figure 9:
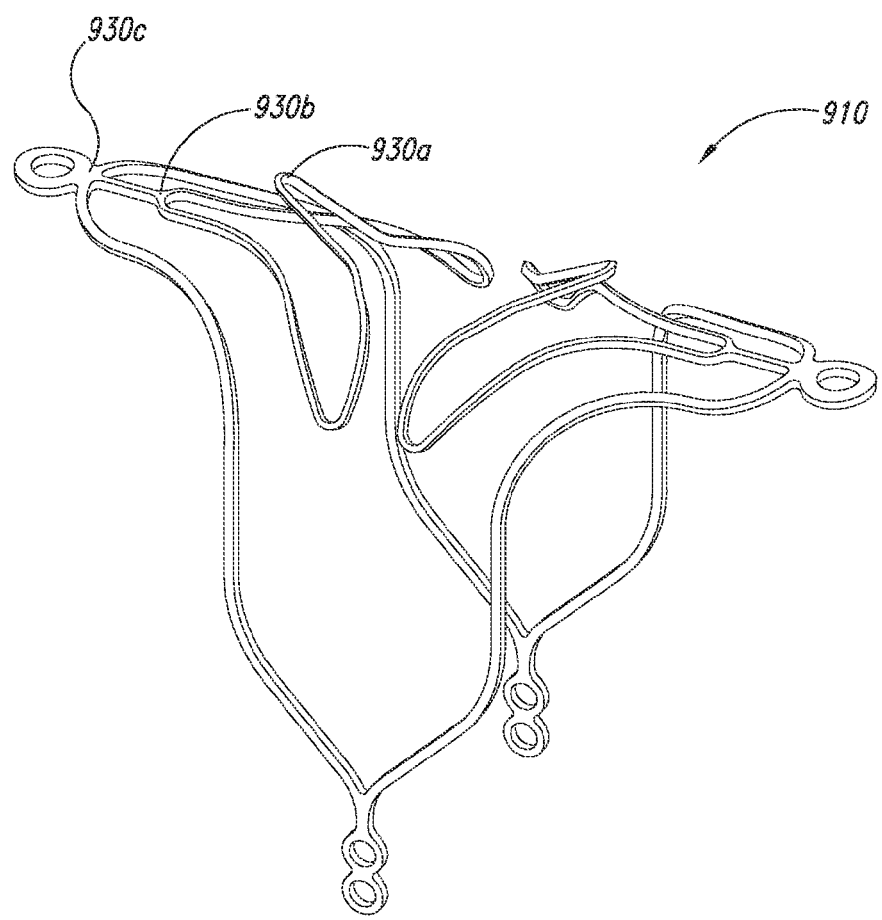
FIG. 9 is an isometric view of a closure structure portion of an aneurysm device configured in accordance with embodiments of the technology.

FIG. 9 is an isometric view of a closure structure portion 910 of an aneurysm device configured in accordance with further embodiments of the technology. Having features generally similar to several of the closure structures described above, the closure structure 910 includes inner, middle, and outer sets of struts (numbered 930a-930c, respectively). In the illustrated embodiment, the inner struts 930a expand or bend distally upward from the laterally-joined middle and outer struts 903b, 903c. This bendability provides a niche between the inner 930a and middle 930b struts. In use, the niche can be used to clip into or otherwise engage the tissue proximate to the aneurysm.

Figure 10A:
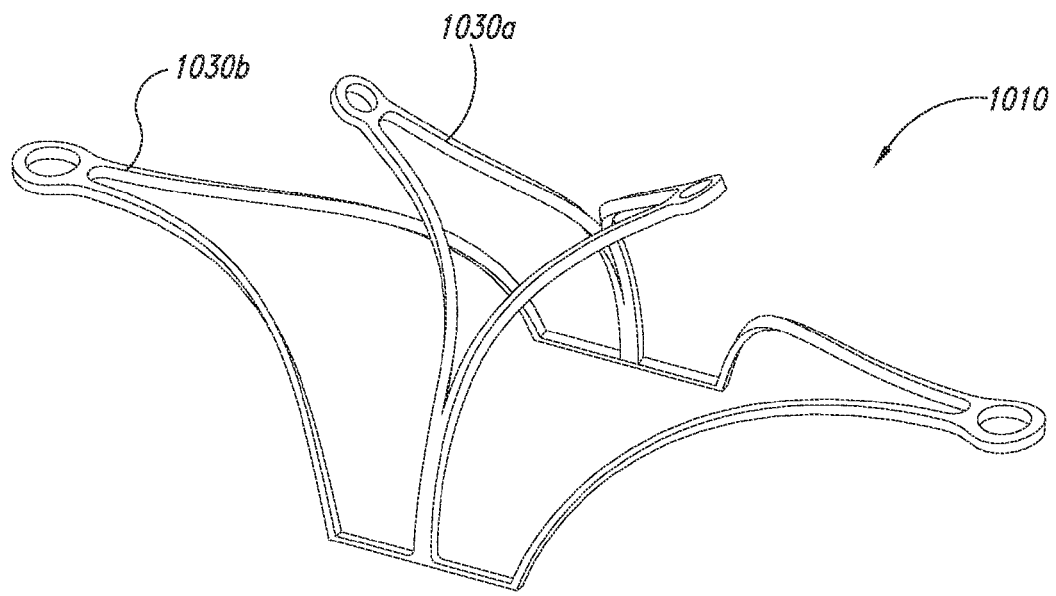
FIGS. 10A and 10B are isometric and front views, respectively, of a closure structure portion of an aneurysm device configured in accordance with embodiments of the technology.
Figure 10B:
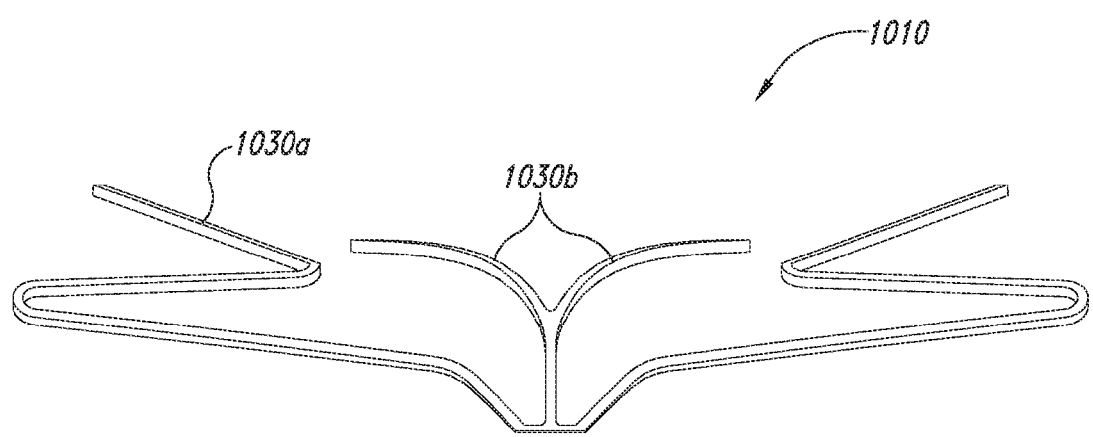

FIGS. 10A and 10B are isometric and front views, respectively, of a closure structure 1010 configured in accordance with embodiments of the technology. The closure structure 1010 includes an inner set of struts 1030a and an outer set of struts 1030b. In some embodiments, the inner set of struts 1030a can be bent or formed in a direction offset from the outer set of struts 1030b to "expand" the aneurysm device 300. In some embodiments, the inner set of struts 1030a can be placed in an aneurysm and the outer set of struts 330b can be placed outside the aneurysm to anchor or stabilize the closure structure 1010 (e.g., to clip the aneurysm device into the aneurysm).

Figure 11A:
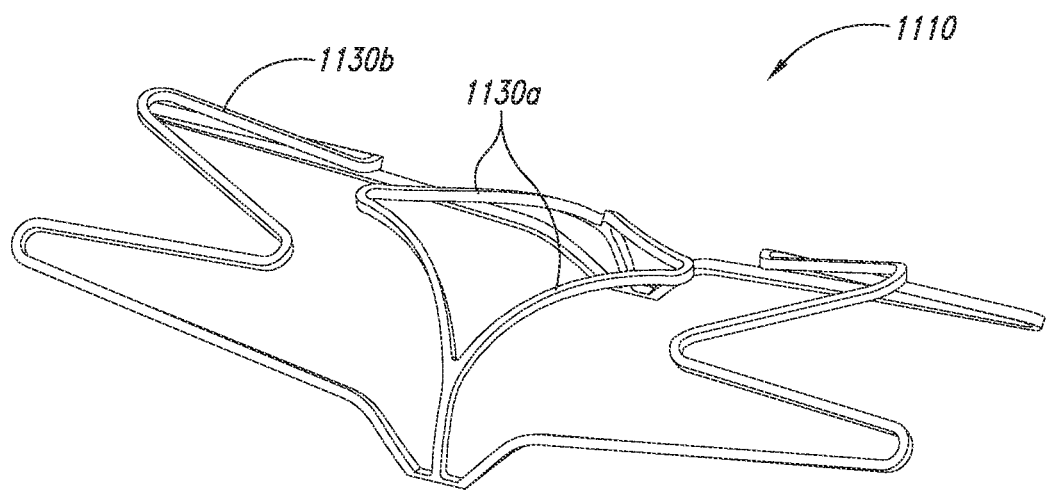
FIGS. 11A and 11B are isometric and top views, respectively, of a closure structure portion of an aneurysm device configured in accordance with embodiments of the technology.
Figure 11B:
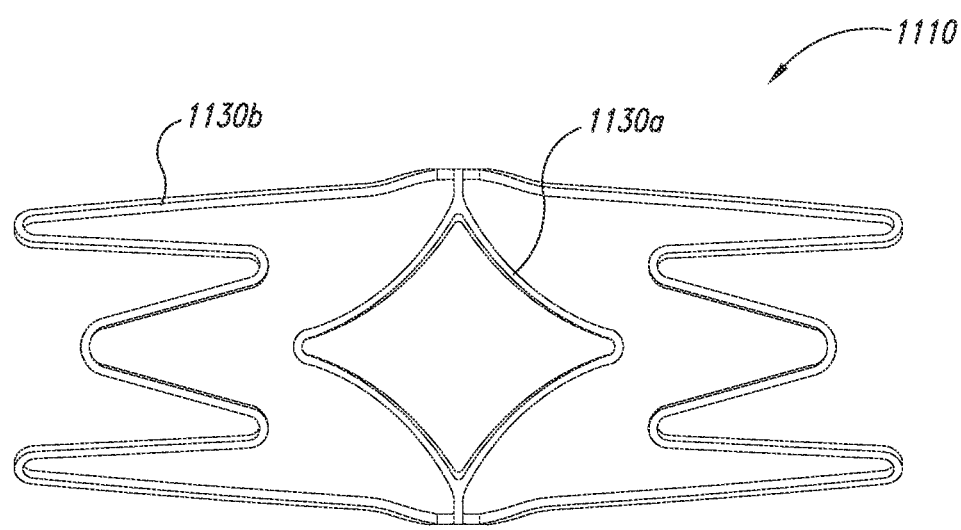

FIGS. 11A and 11B are isometric and top views, respectively, of a closure structure 1110 configured in accordance with embodiments of the technology. The closure structure 1110 includes an inner set of struts 1130a and an outer set of struts 1130b. In some embodiments, the inner set of struts 1130a can be bent or formed in a direction offset from the outer set of struts 1130b. In some embodiments, the inner set of struts 1130a can be placed in an aneurysm and the outer set of struts 1130b can be placed outside the aneurysm for anchoring the closure structure 1110.

FIGS. 12A and 12B are isometric and side views, respectively, of an aneurysm device 1200 configured in accordance with embodiments of the technology. The aneurysm device 1200 includes a closure structure 1210 and a supplemental stabilizer 1220. The closure structure 1210 includes sets of struts 1230a-1230c (collectively, struts 1230) arranged in triangular or rhombus configurations and extending laterally from a midline of the device 1200. As described in several embodiments above, the sets of struts 1230 can rest in or outside an aneurysm, or can sandwich or clip onto the neck of the aneurysm. In the illustrated embodiment, the supplemental stabilizer 1220 includes ring-shaped anchors 1222 extending proximally from the closure structure 1210. These anchors 1222 can be configured to press against vascular walls to provide device stability without blocking blood flow.

FIGS. 13A and 13B are top views an aneurysm device 1300 in an unassembled configuration in accordance with embodiments of the technology. Referring to FIGS. 13A and 13B together, the aneurysm device 1300 is constructed from a substantially flat substrate by cutting, etching, stamping, or otherwise forming the framework of the closure structure 1310 and the unassembled supplemental stabilizer 1320. In several embodiments, the device 1300 can be cut from a single piece of substrate. For example, the closure structure 1310 (including sets of struts 1330a-1330c) and the supplemental stabilizer 1320 can be constructed from a flat sheet of material having substantially uniform thickness. In other embodiments different regions of the sheeted material can have different thicknesses corresponding to the desired thickness for portions of the closure structure 1310 and/or the supplemental stabilizer 1320.

The closure structure 1310 can be folded or bent into a curve along the lateral axis T-T such that the portions of the closure structure 1310 associated with corners 1317a-1317c define paired longitudinally aligned structures on either side and generally substantially orthogonal to the lateral axis T-T. The paired longitudinally aligned structures can be substantially parallel to each other and define anchors that hold the closure structure 1310 in place. The closure structure 1310 forms a vertex that is resiliently bent by a total of about 180° and is biased outward. The outward bias of the closure structure 1310 is due to the materials that form the closure structure, such as resilient metals or alloys including Nitinol and other shape memory metals. The outward biasing force is conveyed to the supplemental stabilizer 1320 from the closure structure 1310 such that the supplemental stabilizer 1320 presses outward against the lumen of a parent vessel that extends at an angle relative to the lengthwise dimension of the closure structure 1310.

Radiopaque markers 1372, 1374, 1376, and 1378 or radiopaque compounds may be associated with certain structures or portions of the device structure to facilitate accurate positioning, placement and monitoring of the deployed device in the vasculature. In one embodiment, for example, a radiopaque composition may be incorporated in the closure structure or provided as a coating on the closure structure. Variations in the marker geometry may be adopted to distinguish different segments of the device framework. For example, the proximal legs of the device may incorporate a marker with two dots, while the portion of the device closer to or in proximity to the covering may incorporate a single dot. Alternatively, different shaped markers may be used to differentiate different parts of the device. Radiopaque markers may be added anywhere along the device frame or attached materials, coverings, and membranes to provide spatial location of different device components and features under angiography. In several embodiments, for example, radiopaque markers can be added to laterally and/or longitudinally asymmetric points on the closure structure 1310 and/or supplemental stabilizer 1320 (i.e., asymmetric with reference to the lateral axis T-T, longitudinal axis L-L, or a center point 1370 at the intersection of the longitudinal and lateral axes). In the embodiment illustrated in FIG. 13A, markers 1372, 1374, 1376, and 1378 are offset from the longitudinal axis L-L. Marker 1372 is offset by distance $X_4$, marker 1374 is offset by distance $X_2$, marker 1376 is offset by distance $X_1$, and marker 1378 is offset by distance $X_3$, where $X_1$, $X_2$, $X_3$, and $X_4$ are all unequal distances. By placing these markers asymmetrically, the markers do not overlap when the device is folded or compressed during placement. The device 1300 is therefore less bulky for delivery.

From the foregoing, it will be appreciated that specific embodiments of the disclosure have been described herein for purposes of illustration, but that various modifications may be made without deviating from the spirit and scope of the disclosure. For example, structures (such as supplemental stabilizers and/or barriers) and/or processes described in the context of particular embodiments may be combined or eliminated in other embodiments. In particular, the aneurysm devices described above with reference to particular embodiments can include one or more additional features or components, or one or more of the features described above can be omitted. Moreover, while advantages associated with certain embodiments of the disclosure have been described in the context of these embodiments, other embodiments may also exhibit such advantages, and not all embodiments need necessarily exhibit such advantages to fall within the scope of the disclosure.

We claim:

1. An aneurysm device endovascularly deliverable to a site proximate an aneurysm, the aneurysm device comprising:
   a closure structure having a distal-facing aspect configured to at least partially occlude the aneurysm, wherein the distal-facing aspect comprises multiple pairs of nested, generally triangular-shaped panels, and further wherein the pairs of panels join at corresponding junctions on a central stem; and a supplemental stabilizer connected to the closure structure, the supplemental stabilizer configured to reside in the artery and press outward against a luminal wall thereof.

2. The aneurysm device of claim 1 wherein each individual panel comprises a framework having an individual barrier material extended thereacross.

3. The aneurysm device of claim 2 wherein the individual barriers have an aperture therethrough.

4. The aneurysm device of claim 3 wherein the closure structure, supplemental stabilizer, and apertures define a longitudinal axis of the device.

5. The aneurysm device of claim 2 wherein the barrier material is permeable.

6. The aneurysm device of claim 2 wherein the barrier material is semi-permeable.

7. The aneurysm device of claim 1 wherein the panels comprise multiple sets of opposing panels, each panel supporting a barrier portion, the opposing panels aligned longitudinally with respect to the artery.

8. The aneurysm device of claim 1 wherein at least one panel is pivotably moveable relative to another panel.

9. The aneurysm device of claim 1 wherein the closure structure is arched and configured to span unobtrusively over the lumina and forms no incursion into the vascular flow path.

10. The aneurysm device of claim 1 wherein the closure structure includes a central hole extending longitudinally through each pair of panels.

11. The aneurysm device of claim 1 wherein the individual panels are shaped and sized to laterally overlap, and wherein, when the closure structure is deployed to at least partially occlude the aneurysm, the panels are configured to control, contain, and/or divert blood flow.

12. The aneurysm device of claim 1 wherein, when the closure structure is deployed to at least partially occlude the aneurysm, at least one panel is configured to be inside the aneurysm and at least one panel is configured to be outside the aneurysm.

* * * * *